United States Patent
Rapoza et al.

(10) Patent No.: US 10,143,572 B2
(45) Date of Patent: Dec. 4, 2018

(54) ASSESSMENT OF A DRUG ELUTING BIORESORBABLE VASCULAR SCAFFOLD

(71) Applicant: Abbott Cardiovascular Systems Inc., Santa Clara, CA (US)

(72) Inventors: Richard Rapoza, San Francisco, CA (US); Susan Veldhof, Rotterdam (NL); James Oberhauser, Saratoga, CA (US); Syed F. A. Hossainy, Hayward, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 704 days.

(21) Appl. No.: 14/121,435

(22) Filed: Sep. 4, 2014

(65) Prior Publication Data
US 2015/0073536 A1   Mar. 12, 2015

Related U.S. Application Data

(60) Provisional application No. 61/967,828, filed on Mar. 26, 2014, provisional application No. 61/893,096, (Continued)

(51) Int. Cl.
*A61L 27/54* (2006.01)
*A61F 2/86* (2013.01)
(Continued)

(52) U.S. Cl.
CPC ................ *A61F 2/86* (2013.01); *A61L 31/06* (2013.01); *A61L 31/148* (2013.01); *A61L 31/16* (2013.01);
(Continued)

(58) Field of Classification Search
None
See application file for complete search history.

(56) References Cited

U.S. PATENT DOCUMENTS

2007/0283552 A1   12/2007   Gale et al.
2008/0275537 A1   11/2008   Limon
(Continued)

OTHER PUBLICATIONS

"Cleveland Clinic study shows two popular statin drugs similarly effective in reversing coronary heard disease", Cleveland Clinic study, 2011, 1 pg.
(Continued)

*Primary Examiner* — Brian Pellegrino
(74) *Attorney, Agent, or Firm* — Squire Patton Boggs (US) LLP

(57) ABSTRACT

A method of treating vascular disease in a patient is disclosed that comprises deploying a bioabsorbable polymer scaffold composed of a plurality of struts at a stenotic segment of an artery of a patient, wherein after the scaffold supports the segment at an increased diameter for a period of time the polymer degrades and is progressively replaced by de novo formation of malleable provisional matrix comprising proteoglycan, wherein as the scaffold becomes more malleable and becomes disconnected as it degrades, wherein following coverage of the struts by a neointima layer and loss of mechanical support provided by the scaffold, the scaffold is pulled outward by positive remodeling of the vessel wall of the scaffolded segment.

10 Claims, 18 Drawing Sheets
(8 of 18 Drawing Sheet(s) Filed in Color)

Related U.S. Application Data filed on Oct. 18, 2013, provisional application No. 61/873,783, filed on Sep. 4, 2013.

(51) Int. Cl.
*A61L 31/14* (2006.01)
*A61L 31/06* (2006.01)
*A61L 31/16* (2006.01)
*A61F 2/915* (2013.01)

(52) U.S. Cl.
CPC ..... *A61F 2/915* (2013.01); *A61F 2002/91558* (2013.01); *A61F 2002/91566* (2013.01); *A61F 2210/0004* (2013.01); *A61F 2250/0067* (2013.01); *A61L 2300/422* (2013.01)

(56) References Cited

U.S. PATENT DOCUMENTS

| | | |
|---|---|---|
| 2010/0004735 A1 | 1/2010 | Yang et al. |
| 2010/0198330 A1 | 8/2010 | Hossainy et al. |
| 2010/0241220 A1* | 9/2010 | McClain ............. A61L 31/10 623/1.42 |
| 2011/0021717 A1 | 1/2011 | Wang et al. |
| 2012/0290070 A1 | 11/2012 | Wang et al. |
| 2013/0317596 A1 | 11/2013 | Rapoza et al. |

OTHER PUBLICATIONS

Dudek et al., "Four-year clinical follow-up of the ABSORB everolimus-eluting bioresorbable vascular scaffold in patients with de novo coronary artery disease: the ABSORB trial", Eurointervention 7, pp. 1060-1061 (2012).

Glagov et al., "Mechanical determinants of plaque modeling, remodeling and disruption", Atherosclerosis 131, Suppl. S13-S14 (1997).

Onuma et al., "Intracoronary optical coherence tomography and histology at 1 month and 2, 3, and 4 years after implantation of everolim us-eluting bioresorbable vascular scaffolds in a porcine coronary artery model", Circulation 122, pp. 2288-2300 (2010).

Serruys et al., "A bioabsorbable everolimus-eluting coronary stent system (ABSORB): 2-year outcomes and results from multiple imaging methods", Lancet 373, pp. 897-910 (2009).

Serruys et al., "Evaluation of the second generation of a bioresorbable everolimus-eluting vascular scaffold for the treatment of de novo coronary artery stenosis", J. of the Am. Coll. of Cadiology, vol. 58, No. 15, pp. 1578-1588 (2011).

Shoenhagen et al., "Arterial remodeling and coronary artery disease:the concept of "dilated" versus "obstructive" coronary atherosclerosis", J. of Am. Coll. of Cardiol. vol. 38, No. 2 (Apendix C) (2001).

\* cited by examiner

TLR = target lesion revascularization, ID = ischemic driven, QCA = quantitative coronary angiography, 1Y = one year, 3Y = three years

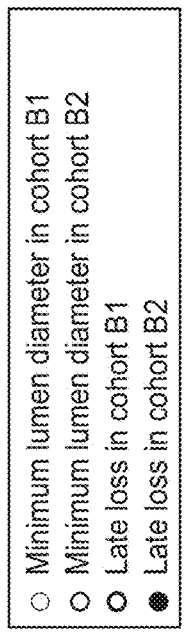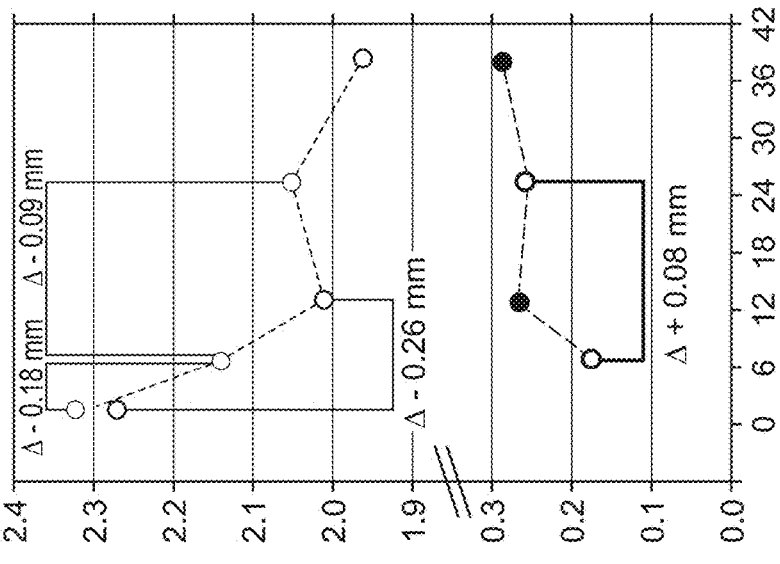
FIG. 3A
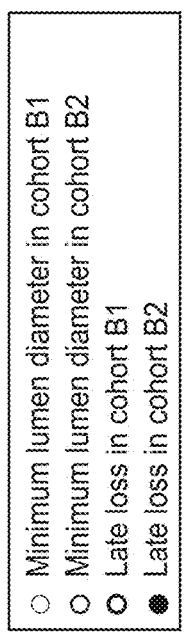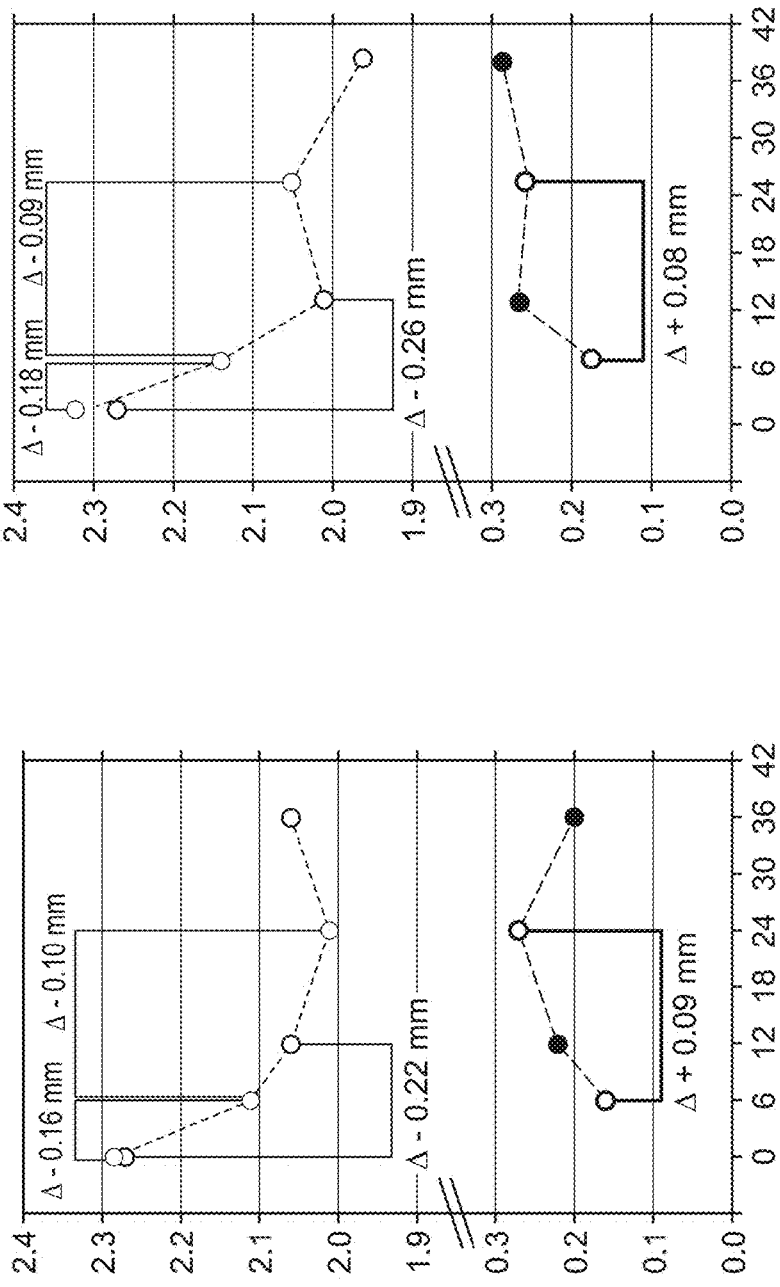
FIG. 3B

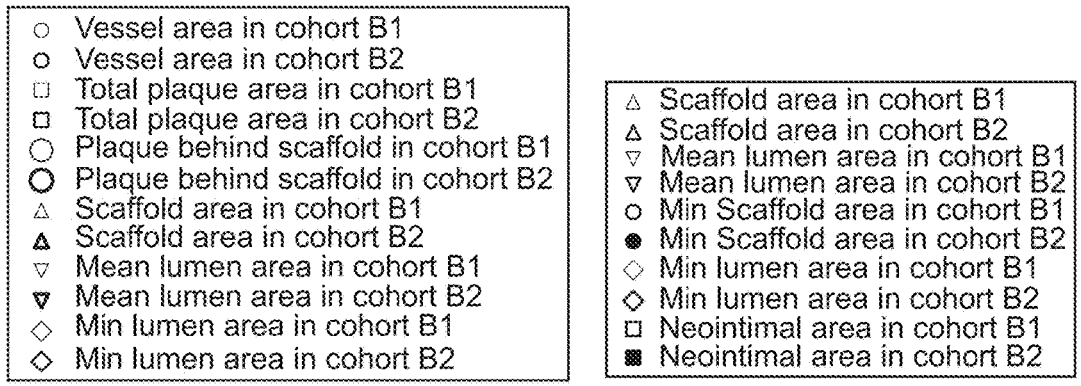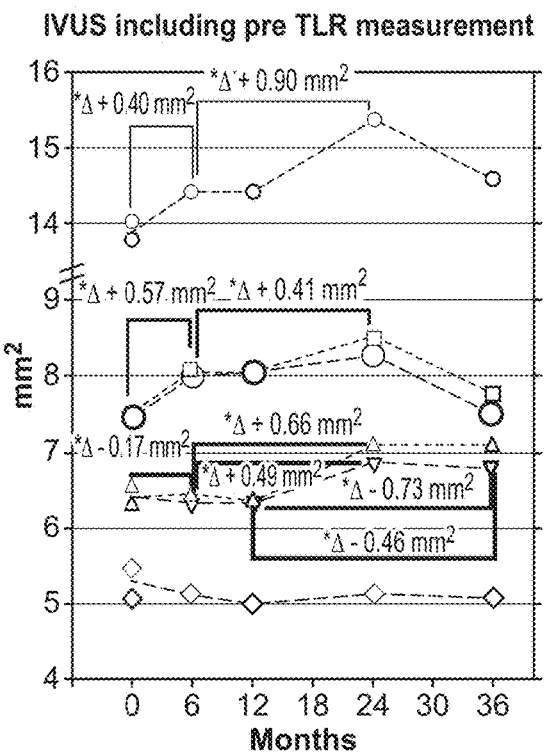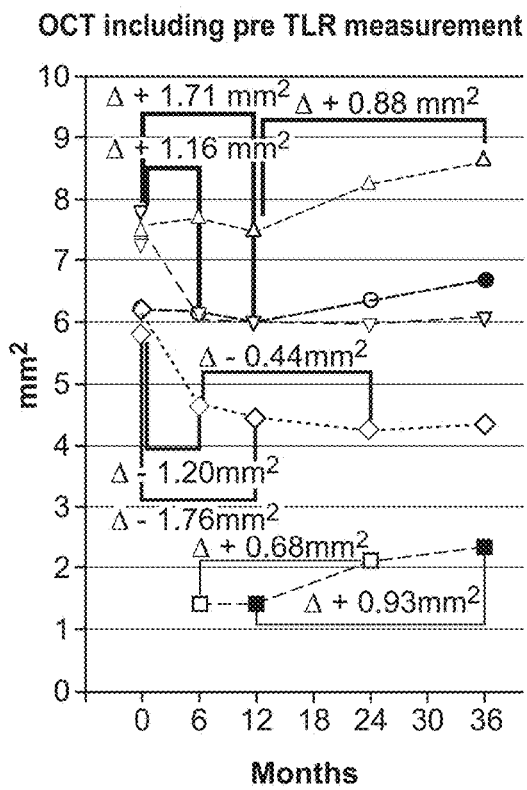
FIG. 3C
FIG. 3D

ASSESSMENT OF A DRUG ELUTING BIORESORBABLE VASCULAR SCAFFOLD

CROSS-REFERENCE TO RELATED APPLICATIONS

This application claims the benefit of U.S. Application Ser. Nos. 61/873,783, filed on Sep. 4, 2013; 61/893,096, filed on Oct. 18, 2013; 61/967,828, filed on Mar. 26, 2014, each of which are incorporated by reference herein.

FIELD OF THE INVENTION

This invention relates to bioresorbable polymer scaffolds and methods of treatment of coronary lesions with bioresorbable polymer scaffolds.

DESCRIPTION OF THE STATE OF THE ART

This invention relates generally to methods of treatment with radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffold gets its name because it physically holds open and, if desired, expands the wall of a passageway in a patient. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must have sufficient radial strength so that it is capable of withstanding the structural loads, namely radial compressive forces imposed on the stent as it supports the walls of a vessel. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded, the stent is expected to yield more severely and only a minimal force is required to cause major deformation.

Once expanded, the stent must adequately provide lumen support during a time required for treatment in spite of the various forces that may come to bear on it, including the cyclic loading induced by the beating heart. In addition, the stent must possess sufficient flexibility with a certain resistance to fracture. The radial strength may be sufficient to support the vessel for at least about 3 months. This may correspond to a radial strength between about 800 and 1300 mm Hg or more narrowly, 900 to 1200 mm Hg. The radial strength value may correspond to scaffold deployed in vivo or in saline.

Stents made from biostable or non-degradable materials, such as metals that do not corrode or have minimal corrosion during a patient's lifetime, have become the standard of care for percutaneous coronary intervention (PCI) as well as in peripheral applications, such as the superficial femoral artery (SFA). Such stents have been shown to be capable of preventing early and later recoil and restenosis.

In order to effect healing of a diseased blood vessel, the presence of the stent is necessary only for a limited period of time, as the artery undergoes physiological remodeling over time after deployment. The development of a bioabsorbable stent or scaffold could obviate the permanent metal implant in vessel, allow late expansive luminal and vessel remodeling, and leave only healed native vessel tissue after the full resorption of the scaffold. Stents fabricated from bioresorbable, biodegradable, bioabsorbable, and/or bioerodable materials such as bioabsorbable polymers can be designed to completely absorb only after or some time after the clinical need for them has ended. Consequently, a fully bioabsorbable stent can reduce or eliminate the risk of potential long-term complications and of late thrombosis, facilitate non-invasive diagnostic MRI/CT imaging, allow restoration of normal vasomotion, provide the potential for plaque regression.

SUMMARY OF THE INVENTION

Embodiments of the present invention include a method of reducing plaque at a segment of a coronary blood vessel comprising an implanted bioabsorbable scaffold in a patient being treated for atherosclerosis, comprising: deploying a bioabsorbable polymer scaffold composed of a plurality of interconnected struts at a stenotic segment of an artery of a patient having a plaque burden, wherein after a period of supporting the segment, the scaffold becomes malleable due to a reduction in radial strength and dismantling of the scaffold caused by biodegradation of scaffold polymer; and administering a plaque burden reducing medication to the patient to reduce the plaque burden between the malleable scaffold and vessel media, the administration made after onset of outward compensatory enlargement of the vessel which prevents malapposition between the malleable scaffold and the vessel media due to outward displacement of the malleable scaffold as the vessel enlarges.

Embodiments of the present invention include a method of restoring vasomotion to a scaffolded segment of a coronary artery treated for stenosis in a patient in need of treatment for restoration of vasomotion comprising: identifying a time period post-deployment of a bioabsorbable scaffold for restoration of vasomotion; selecting a bioabsorbable polymer scaffold having a pressure-displacement property when degrading exhibiting a decrease in outward pressure after an initial yield during the identified time period of degradation; deploying the selected bioabsorbable scaffold at a stenotic segment of the patient and supporting the segment at an increased diameter while restricting vasomotion of the segment; and starting to restore vasomotion to the segment during the identified time period due at least in part to a decrease in outward pressure after yield by the scaffold.

Embodiments of the present invention include a method of stabilizing lumen area of a scaffolded segment of a coronary artery treated for stenosis in a patient in need of treatment for lumen stabilization comprising: selecting or designing a bioabsorbable polymer scaffold having a reduction in radial strength and scaffold discontinuity that enables enlargement of the vessel and scaffold area during a time period post-deployment of a bioabsorbable scaffold in which there is neointimal growth over the struts of the scaffold; deploying the selected bioabsorbable scaffold at a stenotic segment of an artery of the patient which supports the segment at an increased diameter and restricts radial movement of the segment; and restoring freedom of radial movement to the segment and enlarging the vessel and scaffold during the time period, wherein the enlarging of the vessel and scaffold compensates for the growth of neointima over the scaffold during the time period which stabilizes area of the lumen of the segment.

Embodiments of the present invention include A method of treating a stenotic segment of an artery in a patient in need of treatment of atherosclerosis, comprising: restoring normal blood flow through the segment of the artery through deployment of a bioabsorbable polymer scaffold at the stenotic segment to a reference vessel diameter and restricting freedom radial motion, wherein the artery is selected from the group consisting of left coronary (LC), right coronary (RC), posterior non-coronary, and left anterior descending (LAD) and a length of the segment is 12 to 18 mm, restoring freedom of radial motion to the segment after a radial strength of the scaffold decreases below 400 mm Hg and the scaffold develops discontinuities; and stabilizing area of the lumen after restoring freedom of radial motion through enlargement of the vessel which compensates for inward growth of neointimal tissue at the segment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A depicts graphical illustration of the measurements of QCA without pre total lesion revascularization (TLR) performed post procedure, at 6, 12, 24 and 36 months.

FIG. 3B depicts graphical illustration of the measurements of QCA with pre TLR performed post procedure at 6, 12, 24 and 36 months.

FIG. 3C depicts graphical illustration of the measurements of IVUS performed post procedure at 6, 12, 24 and 36 months.

FIG. 3D depicts graphical illustration of the measurements of OCT performed post procedure at 6, 12, 24 and 36 months.

INCORPORATION BY REFERENCE

Figure 1A:
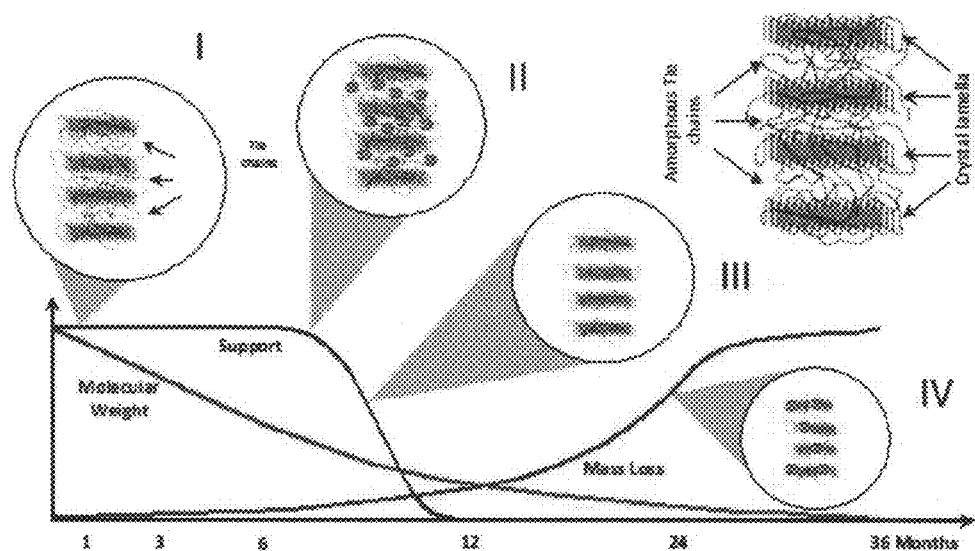
FIG. 1A depicts a bioresorbable vascular scaffold bioresorption process up to 36 months.

All patents, patent publications, patent applications, and other publications referred to herein are incorporated by reference herein for any reason.

DETAILED DESCRIPTION OF THE INVENTION

Various embodiments of the present invention include treatment of coronary artery disease with bioresorbable polymer stents. The bioresorbable stents can include a support structure in the form of a scaffold made of a material that is bioresorbable, for example, a bioresorbable polymer such as a lactide-based polymer. The scaffold is designed to completely erode away from an implant site after treatment of an artery is completed. The scaffold can further include a drug, such as an antiproliferative or anti-inflammatory agents. A polymer coating disposed over the scaffold can include the drug which is released from the coating after implantation of the stent. The polymer of the coating is also bioresorbable.

Embodiments of the present invention include deploying a bioabsorbable polymer scaffold composed of a plurality of struts at a stenotic segment of an artery of a patient that has been shown to exhibit any combination of the clinical results, animal study results, and bench results.

The present invention is applicable to, but is not limited to, self-expandable stents, balloon-expandable stents, stent-grafts, and generally tubular medical devices in the treatment of artery disease. The present invention is further applicable to various stent designs including wire structures, and woven mesh structures.

Self expandable or self expanding stents include a bioabsorbable polymer scaffold that expands to the target diameter upon removal of an external constraint. The self expanding scaffold returns to a baseline configuration (diameter) when an external constraint is removed. This external constraint could be applied with a sheath that is oriented over a compressed scaffold. The sheath is applied to the scaffold after the scaffold has been compressed by a crimping process. After the stent is positioned at the implant site, the sheath may be retracted by a mechanism that is available at the end of the catheter system and is operable by the physician. The self expanding bioabsorbable scaffold property is achieved by imposing only elastic deformation to the scaffold during the manufacturing step that compresses the scaffold into the sheath.

The bioabsorbable scaffold may also be expanded by a balloon. In this embodiment, the scaffold is plastically deformed during the manufacturing process to tightly compress the scaffold onto a balloon on a catheter system. The scaffold is deployed at the treatment site by inflation of the balloon. The balloon will induce areas of plastic stress in the bioabsorbable material to cause the scaffold to achieve and maintain the appropriate diameter on deployment.

A stent scaffold can include a plurality of cylindrical rings connected or coupled with linking elements. For example, the rings may have an undulating sinusoidal structure. When deployed in a section of a vessel, the cylindrical rings are load bearing and support the vessel wall at an expanded diameter or a diameter range due to cyclical forces in the vessel. Load bearing refers to the supporting of the load imposed by radial inwardly directed forces. Structural elements, such as the linking elements or struts, are generally non-load bearing, serving to maintain connectivity between the rings. For example, a stent may include a scaffold composed of a pattern or network of interconnecting structural elements or struts.

Figure 10:
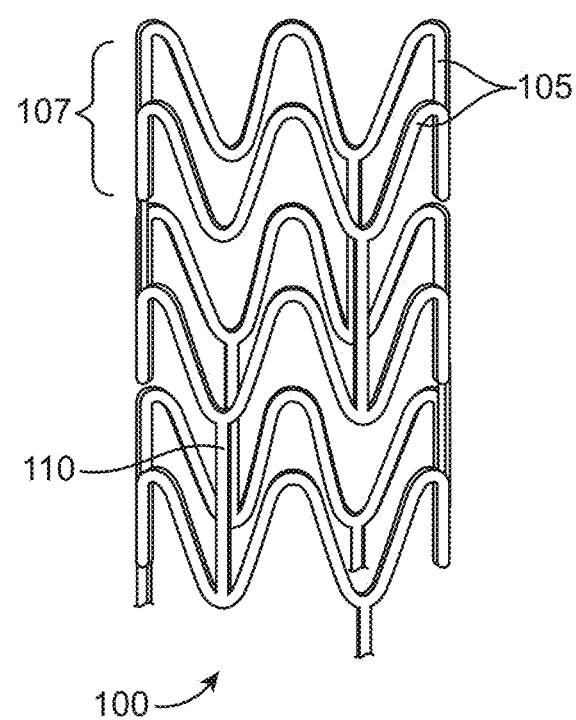
FIG. 10 depicts an exemplary stent scaffold.

FIG. 10 depicts a view of an exemplary stent 100. In some embodiments, a stent may include a body, backbone, or scaffold having a pattern or network of interconnecting structural elements 105. Stent 100 may be formed from a tube (not shown). FIG. 10 illustrates features that are typical to many stent patterns including undulating sinusoidal cylindrical rings 107 connected by linking elements 110. As mentioned above, the cylindrical rings are load bearing in that they provide radially directed force to support the walls of a vessel. The linking elements generally function to hold the cylindrical rings together. A structure such as stent 100 having a plurality of structural elements may be referred to as a stent scaffold or scaffold. Although the scaffold may further include a coating, it is the scaffold structure that is the load bearing structure that is responsible for supporting lumen walls once the scaffold is expanded in a lumen.

The structural pattern in FIG. 10 is merely exemplary and serves to illustrate the basic structure and features of a stent pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 10, can be formed on a tube or sheet with a technique such as laser cutting or chemical etching. The stent can then be crimped on to a balloon or catheter for delivery into a bodily lumen. Alternatively, the scaffold design may be composed of radial bands that slide to increase the diameter of the scaffold. Such a design utilizes a locking mechanism to fix the stent at a target diameter and to achieve final radial strength. In other embodiments, the scaffold design could be braided polymer filaments or fibers.

The treatment methods disclosed herein can apply to bioresorbable scaffolds for both coronary and peripheral treatment. Bioresorbable polymer scaffolds for coronary artery treatment can have a length between 12 to 18 mm. Such coronary scaffolds may be laser cut from polymer tubes with a diameter between 2.5 mm to 4.5 mm and with a thickness/width of 140-160 microns.

The coronary scaffold may be configured for being deployed by a non-compliant or semi-compliant balloon from about a 1.1 to 1.5 mm diameter (e.g., 1.35 mm) crimped profile. Exemplary balloon sizes include 2.5 mm, 3.0 mm, 3.5 mm, and 4.0 mm, where the balloon size refers to a nominal inflated diameter of the balloon. The scaffold may be deployed to a diameter of between 2.5 mm and 5 mm, 2.5 to 4.5 mm, or any value between and including the endpoints. The pressure of the balloon to deploy the scaffold may be 12 to 20 psi. Embodiments of the invention include the scaffold in a crimped diameter over and in contact with a deflated catheter balloon.

The intended deployment diameter may correspond to, but is not limited to, the nominal deployment diameter of a catheter balloon which is configured to expand the scaffold. The balloon pressure and the diameter to which the balloon inflates and expands the scaffold may vary from deployment to deployment. For example, the balloon may expand the scaffold in a range between the nominal inflated diameter to the nominal inflated diameter plus 0.5 mm, e.g., a 3.0 mm balloon may expand a scaffold between 3 and 3.5 mm. In any case, the inflated diameter at deployment is less than the rated burst diameter of the balloon.

A scaffold may be laser cut from a tube (i.e., a pre-cut tube) that is less than an intended deployment diameter. In this case, the pre-cut tube diameter may be 0.7 to 1 times the intended deployment diameter or any value or range in between and including the endpoints.

Compared with bare metal stents, drug-eluting stents (DES) that are not bioresorbable have been shown to be safe and to result in greater absolute reductions in target lesion revascularization (TLR) and target vessel revascularization. A DES refers to a stent including a support structure (e.g., scaffold) and also includes a drug eluting coating over the support structure. The coating can include a polymer and a drug. The polymer functions as a drug reservoir for delivery of the drug to a vessel. The polymer can be non-biodegradable or bioresorbable. The DES that are not bioresorbable include a metal support structure with a drug eluting coating.

The ABSORB Bioresorbable everolimus eluting vascular scaffold (ABSORB BVS) of Abbott Vascular Inc. of Santa Clara, Calif. was developed to provide an approach to treating coronary artery lesions with transient vessel support and drug delivery. Preclinical evaluation in an animal model demonstrated substantial polymer degradation at 2-years post ABSORB BVS implantation, with complete disappearance of the BVS strut "footprint" in the vessel wall within a 3-4 year period. The first generation BVS (BVS revision 1.0) was tested in the ABSORB cohort A trial and demonstrated promising results with a low event clinical rate at up to 4 years follow up (EuroIntervention 2012; 7:1060-1061). The device was however limited by a slightly higher acute recoil compared to conventional metallic platform stents.

Improvements in design described herein were introduced in the second generation BVS (BVS revision 1.1), notably an enhanced mechanical strength, more durable support to the vessel wall, a reduced maximum circular unsupported surface area and a more uniform strut distribution and drug delivery. The performance of the next generation BVS revision 1.1 was subsequently investigated in the ABSORB Cohort B Trial which reported excellent clinical results at 1 and 2 year follow-up (J Am Coll Cardiol. 2011; 58: B66).

The polymer backbone is made of poly(L-lactide). The diameter of the scaffold is 3 mm and the length is 18 mm. The struts have a width of about 165 microns and thickness of about 152 microns. The coating is a mixture of poly(DL-lactide) and everolimus with a 1:1 ratio of polymer to drug. The coating is about 2 to 2.5 microns in thickness. The drug dose density is 100 µg/cm$^2$, which is the drug mass per scaffold surface area. The surface area of the scaffold is 160 mm$^2$, so the target drug dose is about 160 µg. The surface area of the scaffold per unit scaffold length is about 8.9 mm$^2$/mm.

Figure 11:
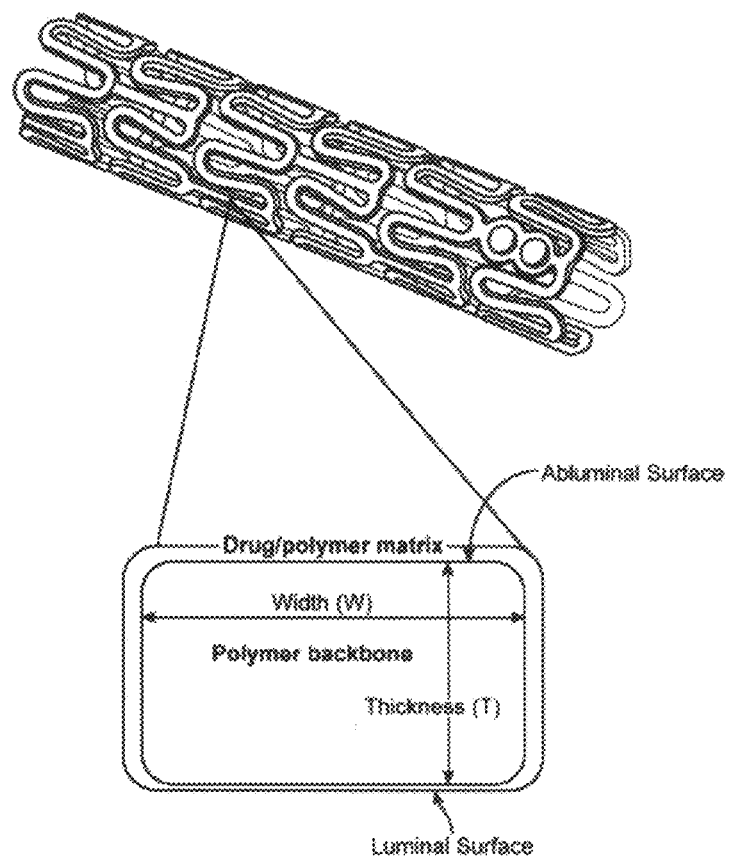
FIGS. 11A-B depicts a bioresorbable vascular scaffold (BVS).

FIGS. 11A-B depicts the BVS revision 1.1 scaffold. FIG. 11A shows the scaffold in a crimped configuration. FIG. 11B show a cross-selection of a strut showing the polymer backbone or core of the strut surrounded by a drug/polymer matrix. The cross-section of the strut has an abluminal surface or side that faces the vessel wall and a luminal surface or side that faces the lumen of the vessel. The strut cross-section shown is rectangular with rounded corners with a width (W) and thickness (T). The BVS revision 1.1 scaffold is approximately square with an aspect ratio T/W close to 1.

Figure 12:
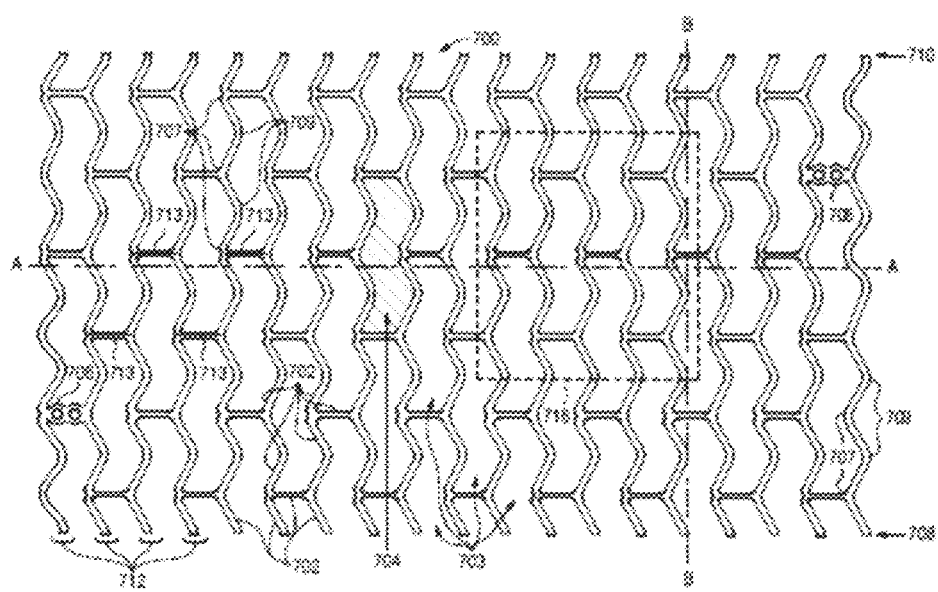
FIG. 12 depicts an exemplary stent pattern shown in a planar or flattened view.

In a preferred embodiment a scaffold for coronary applications has the stent pattern described in U.S. application Ser. No. 12/447,758 (US 2010/0004735) to Yang & Jow, et al. Other examples of stent patterns suitable for PLLA are found in US 2008/0275537. FIG. 12 depicts exemplary stent pattern 700 from US 2008/0275537. The stent pattern 700 is shown in a planar or flattened view for ease of illustration and clarity, although the stent pattern 700 on a stent actually extends around the stent so that line A-A is parallel or substantially parallel to the central axis of the stent. The pattern 700 is illustrated with a bottom edge 708 and a top edge 710. On a stent, the bottom edge 708 meets the top edge 710 so that line B-B forms a circle around the stent. In this way, the stent pattern 700 forms sinusoidal hoops or rings 712 that include a group of struts arranged circumferentially. The rings 712 include a series of crests 707 and troughs 709 that alternate with each other. The sinusoidal variation of the rings 712 occurs primarily in the axial direction, not in the radial direction. That is, all points on the outer surface of each ring 712 are at the same or substantially the same radial distance away from the central axis of the stent.

The stent pattern 700 includes various struts 702 oriented in different directions and gaps 703 between the struts. Each gap 703 and the struts 702 immediately surrounding the gap 703 define a closed cell 704. At the proximal and distal ends of the stent, a strut 706 includes depressions, blind holes, or through holes adapted to hold a radiopaque marker that allows the position of the stent inside of a patient to be determined.

One of the cells 704 is shown with cross-hatch lines to illustrate the shape and size of the cells. In the illustrated embodiment, all the cells 704 have the same size and shape. In other embodiments, the cells 704 may vary in shape and size.

Still referring to FIG. 12, the rings 712 are connected to each other by another group of struts that have individual lengthwise axes 713 parallel or substantially parallel to line A-A. The rings 712 are capable of being collapsed to a smaller diameter during crimping and expanded to their original diameter or to a larger diameter during deployment in a vessel. Specifically, pattern 700 includes a plurality of hinge elements 731, 732, 733, 734. When the diameter of a stent having stent patter 700 is reduced or crimped, the angles at the hinge elements decrease which allow the diameter to decrease. The decrease in the angles results in a decrease in the surface area of the gaps 703. In general, for most coronary applications, the diameter of the scaffold in an as-fabricated or pre-crimped configuration is 2 to 5 mm, or more narrowly 2.5 to 3.5 mm. In general, the length of the scaffold is 8 to 38 mm, or more narrowly, 8 to 12 mm, 12 to 18 mm, 18 mm to 38 mm. The scaffold for may be configured for being deployed by a non-compliant balloon, e.g., 2.5 to 4 mm diameter, from about a 1.8 to 2.2 mm diameter (e.g., 2 mm) crimped profile. The coronary scaffold may be deployed to a diameter of between about 2.5 mm and 4 mm.

The present application includes results and analysis from the ABSORB Cohort B Trial. Observations with multi-modality imaging of the Absorb bioresorbable everolimus-eluting vascular scaffold have been performed in two consecutive cohorts of patients who were serially investigated either at 6 and 24 months or at 12 and 36 months. US2013/0317596A1 also discloses the scaffold and clinical results.

In the Absorb multicenter single-arm trial, 45 patients (Cohort B1) and 56 patients (Cohort B2, n=56) underwent serial invasive imaging, specifically quantitative coronary angiography (QCA), intravascular ultrasound (IVUS), radio-frequency backscattering and optical coherence tomography (OCT). The patients of the ABSORB Cohort B trial were divided into 2 groups, Cohort B1 (n=45) with imaging follow-up at 180 days and 2 years and Cohort B2 (n=56) with imaging follow-up at 1 and 3 years. A 5 year imaging follow-up was performed in both cohorts. Results of 24/45 patients in B1 who agreed to return for 5 year imaging are disclosed herein.

Between one and 3 years, late luminal loss remained unchanged (6 months: 0.19 mm, 1 year: 0.27 mm, 2 year: 0.27 mm, 3 years: 0.29 mm) and the in-segment angiographic restenosis rate for the entire Cohort B (n=101) at 3 years was 6%. On IVUS, mean lumen, scaffold, plaque and vessel area showed significant enlargement between one and 2 years. Mean lumen and scaffold area remained stable between 2 and 3 years whereas significant reduction in plaque behind the struts occurred with adaptive restrictive remodeling of the external elastic membrane (EEM) or lamina. Hyperechogenicity of the vessel wall, a surrogate of the bioresorption process, decreased from 23.1% to 10.4% with a reduction of radiofrequency backscattering for dense calcium and necrotic core (p<0.001). At 3 years, the count of strut cores detected on OCT increased significantly, probably reflecting the dismantling of the scaffold; 98% of struts were covered. In the entire Cohort B (n=101), the 3-year major adverse cardiac event rate was 10.0% without any scaffold thrombosis.

The current investigation demonstrated the dynamism of vessel changes after implantation of a bioresorbable scaffold, resulting at 3 years in stable luminal dimensions, low restenosis rate and low clinical major adverse cardiac event rates.

Bioresorbable scaffolds have to face multiple challenges which justify the careful evaluation of this novel technology. First of all the polymeric scaffolds have to match the mechanical properties of metallic stents. It has been demonstrated that the acute recoil of a novel scaffold was not inferior to the one observed with an equivalent device in metal. Secondly, it has been established in human testing that the mechanical integrity and the absence of recoil were maintained over a period of 6 months. During that time lapse the biological process of restenosis, consisting of neointimal formation and constrictive remodeling fully subsides and therefore does not justify a permanent metallic prosthesis. In the following months, it has been shown that physiological and pharmacological vasomotion reappear confirming the fact that the scaffold loses its mechanical stiffness as the amorphous tie chains between crystal lamellae of polylactide are hydrolyzed (FIG. 1A).

FIG. 1A depicts a schematic representation of time dependent degradation behavior of a bioabsorbable scaffold after intervention or deployment. The time scale shown is exemplary, the time dependence of scaffold behavior is a qualitative representation. Specifically, FIG. 1A shows the time dependence of the molecular weight of the scaffold material, the radial strength of the scaffold, and the mass loss from the scaffold due to bioresorption of the scaffold material. FIG. 1A also shows schematic depictions of the hypothesized molecular structure of the semicrystalline polymer scaffold material and the change in the structure as the material degrades. As shown by (I), the polymer scaffold material includes crystallites or crystal lamella (load bearing elements) connected by amorphous polymer tie chains (binders). As illustrated in (II), polymer hydration or water penetration into the scaffold material follows implantation. The water causes depolymerization of the material by hydrolysis which preferentially cleaves amorphous tie chains, leading to a decrease in molecular weight without altering radial strength. As shown in (III), it is believed that polymer fragmentation into segments of low molecular weight polymer due to the scission of amorphous tie chains linking the crystalline regions, results in this subsequent gradual loss of the radial strength. Referring to (IV), mass loss begins when oligomers are sufficiently small to escape the matrix and be resorbed into the tissue. The soluble monomer (e.g. L-lactate) is changed into pyruvate which eventually enters the Krebs cycle and is further converted into carbon dioxide and water, eliminated by the lungs and kidneys.

Figure 1B:
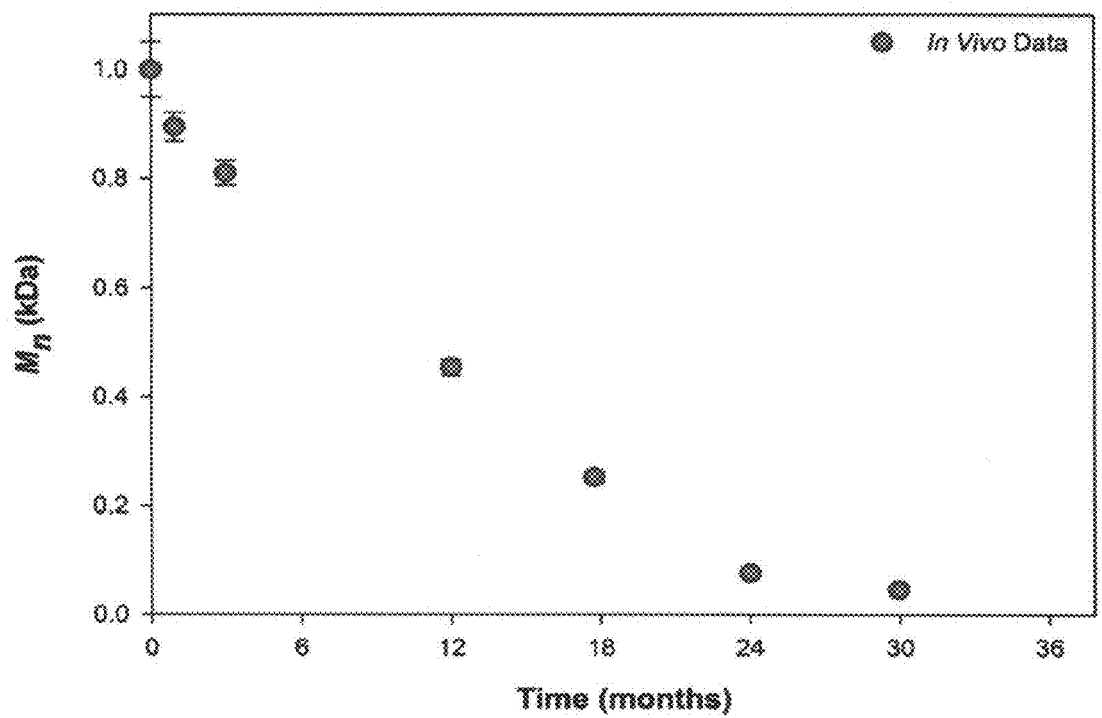
FIG. 1B depicts in vivo data for a bioresorbable vascular scaffold made of poly(L-lactide) (PLLA).
Figure 1C:
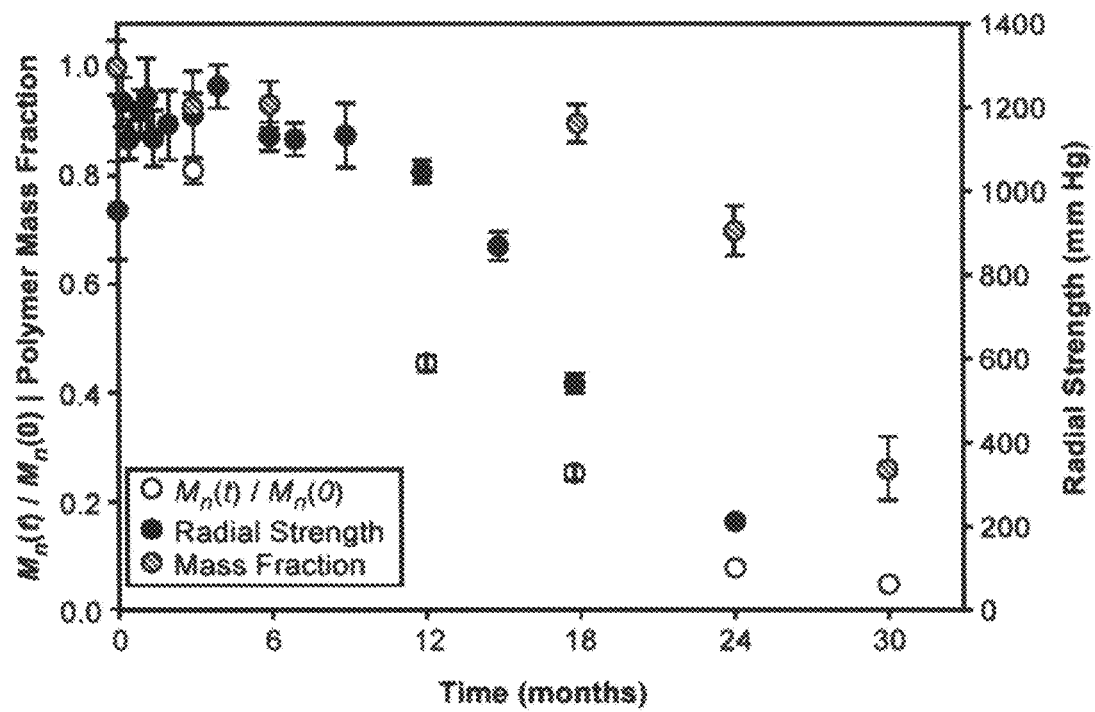
FIG. 1C depicts the normalized molecular weight along with the radial strength, and mass fraction, mass (t)/mass (t=0) versus time for a degrading PLLA scaffold.

FIGS. 1B-C depict in vivo and in vitro data for a bioresorbable vascular scaffold made of poly(L-lactide). FIG. 1B shows the normalized molecular weight ($Mn(t)/Mn(t=0)$). FIG. 1C depicts the normalized molecular weight along with the radial strength, and mass fraction, mass $(t)/mass(t=0)$ versus time for a degrading PLLA scaffold.

The normalized molecular weight and mass fraction data are in vivo data obtained by implanting the scaffolds in pigs and explanting the samples at time points between t=0 and 30 months.

The coronary arteries of non-diseased swine were implanted with a single Absorb scaffold at a targeted 1.1:1 balloon: artery ratio. Arteries were evaluated at 1, 3, 6, 12, 18, 24, 30, 36, and 42 months by light microscopy (LM) (n=10-13/time point) or gel permeation chromatography (GPC) (n=8-14/time point). Arteries evaluated by LM also were assessed in vivo with intravascular ultrasound (IVUS) at explant. In total, 101 arteries were evaluated histologically and 99 arteries were evaluated by IVUS at follow-up time points from 1 to 42 months post-Absorb implantation.

For Light Microscopy (LM), preparation of implanted arteries for plastic embedding and histomorphological evaluation followed standard procedures. Arteries were divided into 3 blocks representing the proximal, mid, and distal regions. A 4-6 μm section from each block was collected and stained with Movat's pentachrome for histomorphometrical evaluation by computerized planimetry (Image-Pro Plus software, MediaCybernetics, Rockville, Md.).

For IVUS, pullbacks were acquired at an automated pullback rate of 1.0 mm/s (Boston Scientific Galaxy II system or iLab Ultrasound Imaging System, 40 Mz catheter, Natick, Mass.). Three representative still frames from the proximal, mid, and distal regions of the implanted segment and the proximal and distal reference vessel within 2 mm of the implanted segment were captured in the end diastolic state. In addition, a frame of the mid implant in the end systolic state was captured. Lumen area (LA) was measured in each collected still frame.

For GPC, a previously reported GPC method, with a slightly modified sample extraction/purification process, was employed to investigate the degradation of polymer over time as it relates to the number-average molecular weight (Mn) (Onuma Y, Serruys P, et al. Circulation 122 (22): 2288-2300, 2010). Extraction and purification of the polymer was repeated up to five times until the polymer was fully extracted from the tissue (i.e., the polymer signal below the quantitation limit of 0.3 mg/mL). Samples were analyzed prior to device implantation (T0) and at follow-up from 1 to 42 months. The Mn of polymer was calculated from the calibration curves obtained for polystyrene standards (Mw range, 500-700,000 Da), whereas the amount of polymer was calculated from the calibration curves constructed by five calibration standards (0.3-4.0. mg/mL) of polylactide (PDLLA) certified reference material with a Mw of 90,000 Da. FIG. 1B depicts the GPC assessment of $M_n/M_{n,0}$ versus time for Absorb implanted in porcine coronary arteries. FIG.

1B shows that at 12 months, Absorb demonstrates a 49% decrease in numeric average molecular weight (Mn).

The radial strength data was obtained by deploying samples to nominal product diameter in a phosphate buffered saline (PBS) solution at 37° C. and holding under these conditions out to time points of 18 months. After removal from the PBS solution, the scaffolds were inspected for structural integrity prior to testing for circumferential radial strength at 37° C. using an MSI RX550 radial force tester (Machine Solutions Inc., Flagstaff, Ariz.). Pressure-diameter curves were obtained and analyzed both quantitatively for a radial strength value and qualitatively for curve shape. It is expected that the measured radial strength is not sensitive to an in vitro or in vivo environment. Table 1 summarizes the changes in scaffold properties during degradation periods between t(0) and selected degradation times. As shown in FIG. 1C, the normalized MW is less than 0.5 (about 0.48) at 12 months and less than 0.1 (about 0.1) at 30 months.

The radial strength value on the t=0 line is about 960 mm and the value shortly after t=0 is about 1200 mm Hg. The increase is likely due to plasticization of the scaffold polymer. The initial radial strength is taken to be about 1200 mm Hg so the change in radial strength will be based on this value. The radial strength varies by less than about 2% from this initial value during the first three months. After six months, the radial strength varies as follows: 6 months—about 1150 mm Hg (96% of initial); 9 months—about 1160 mm Hg (96% of initial); 12 months—about 1090 mm Hg (92% of initial); 15 months—about 890 mm Hg (75% of initial); 18 months—about 560 mm Hg (47% of initial); and 24 months—about 220 mm Hg (18% of initial).

The mass fraction decreases by less than 5% during the first 6 months and decreases to about 0.9 after 18 months. At 30 months the mass fraction is about 0.28.

pressure after the initial yield point rather than strain-hardening behavior. At 12 months the scaffold exhibits less resistance to radial compression as compared to prior time points. This change is more pronounced between 12 and 15 months, however, some change is observed between 9 and 12 months. This dramatic change at 15 months is consistent with the reduced resistance of the scaffold to an applied radial load.

Without being bound by theory, the change in behavior between 9 and 12 months may be due to cracking or some other form of stress relief. The change may be correlated to the change in the amount and type of support the vessel is receiving from the scaffold and is indicative of a transition in scaffolding behavior leading to the restoration of vasomotion.

The above data may provide guidance in treating a coronary lesion, in particular, the restoring of vasomotion. A method for restoring vasomotion to a scaffolded segment of a coronary artery may include identifying a time period post-deployment of a bioabsorbable scaffold for restoration of vasomotion. A bioabsorbable polymer scaffold may be selected that has a pressure-displacement property when degrading in a fluid that shows a decrease in outward pressure after an initial yield during the identified time period during the degrading. The selected scaffold may be deployed at a stenotic segment of the patient which supports the segment at an increased diameter and restricts vasomotion of the segment. The scaffold may start to restore vasomotion to the segment during the time period due at least in part to the decrease in pressure of the scaffold. For example, the time period is between 9 and 12 months, between 9 and 15 months, or between 12 and 15 months.

The scaffold may be designed to exhibit pressure-displacement property at any selected time period during which

TABLE 1

Summary of changes in scaffold properties during degradation periods.

| Scaffold Property | Change t(0)-1 Y | Change t(0)-1.5 Y | Change (t(0)-2 Y | Change t(0)-2.5 Y | Change 1 Y-2 Y | Change 1-2.5 Y |
| --- | --- | --- | --- | --- | --- | --- |
| Mn(t)/Mn(0) | −52% | −78% | −92% | −95% | −81% | −90% |
| Radial Strength | −8% | −53% | −83% | — | −81% | — |
| Mass Fraction | — | −8% | −30% | −78% | — | — |

Figure 13:
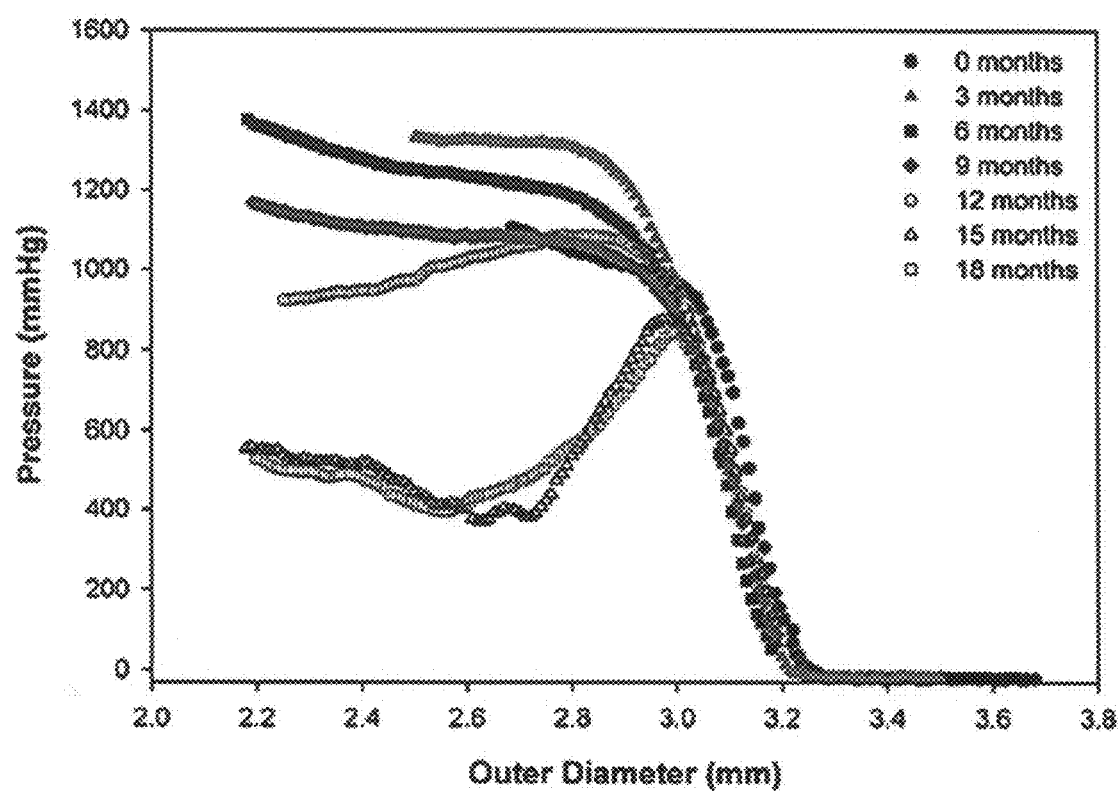
FIG. 13 depicts pressure-diameter curves of the Absorb at different soaking times in phosphate buffered saline (PBS) solution.

FIG. 13 depicts the pressure-diameter or pressure-displacement curves of the scaffolds soaked in the PBS solution for different soaking times. Each curve (i.e., each set of points of a given color/symbol) represents a single sample, tested on an iris crimping machine. The scaffold is disposed within the iris and the iris closes from 3.7 mm to 2.2 mm. The curves are representative curves for each soak time. As the iris is closing, the machine records a pressure value at each position.

As the iris contacts the sample, there is a steep rise in the pressure curve, which is comparable to an elastic region in a typical stress/strain curve. After the yield point, for the shorter soak times (0, 3, 6, 9 months) a plastic region which exhibits strain hardening is observed. Strain-hardening refers to strain strengthening of a material subjected to plastic deformation. For strain-hardened materials, the yield stress increases with increasing plastic deformation.

The curves exhibit a marked change in shape between 9 and 12 months. At higher soak times, 12 months and beyond, a decrease in pressure (stress) after the yield point is observed. The change in shape demonstrates a decrease in it is desired to start the restoration of vasomotion. It is believed that the pressure-displacement property depends on the degradation rate, radial strength, and fracture toughness of the scaffold. These scaffold properties and thus the pressure-displacement property can be adjusted to obtain a selected time period for start of vasomotion. The adjusting can be performed through selection of scaffold material and adjustment of properties such as crystallinity and biaxial orientation by modulating processing techniques, as described in US 2010/0198330, US 2011/0021717, and US 2012/0290070. The time period can be selected or adjusted, for example, to be between 3 and 6 months or between 6 and 9 months.

The Mn at the start of restoration of vasomotion may be may be less than 50 kDa, less than 40 kDa, less than 30 kDa, less than 20 kDa, 20 to 50 kDa, 30 to 40 kDa, or 20 to 40 kDa. Alternatively, or additionally, the radial strength may be less than 700, less than 500 mm Hg, less than 300 mm Hg, less than 100 mm Hg, less than 30 mm Hg; 300 to 500 mm Hg, or 200 to 700 mm Hg. The plaque burden reducing medication may be a statin.

Figure 14:
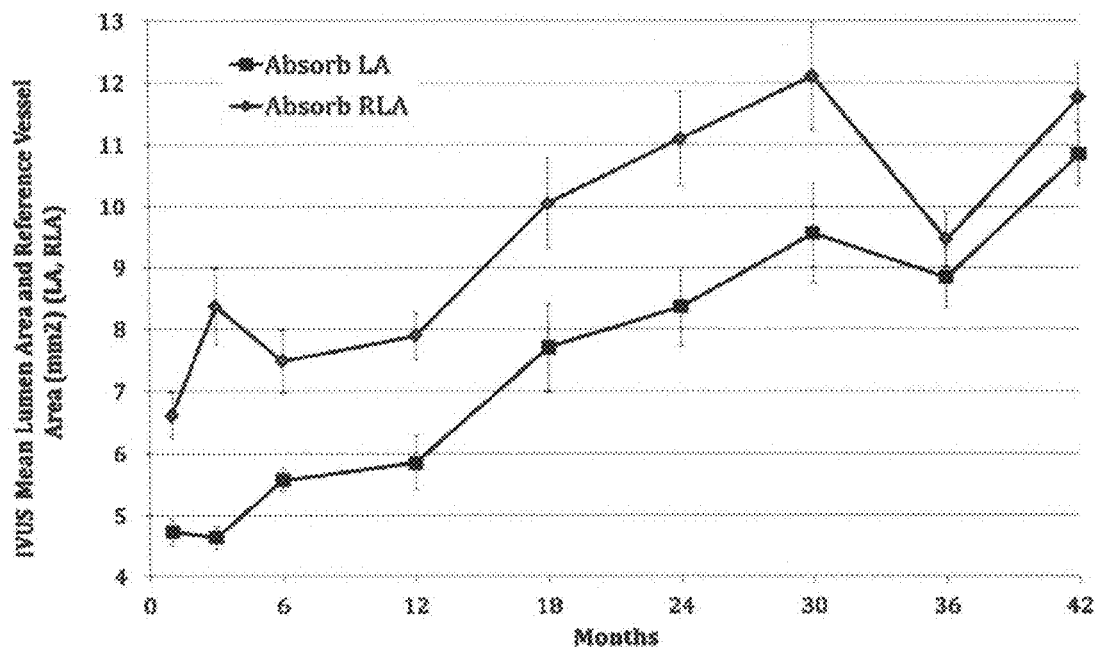
FIG. 14 depicts IVUS Lumen Area (LA) and reference vessel area (RLA) for Absorb implanted arteries from 1 to 42 months.

FIG. 14 depicts IVUS Lumen Area (LA) and reference vessel area (RLA) for Absorb implanted arteries from 1 to 42 months. At 12 months and later time points, there is a progressive increase in lumen area (LA) that corresponds to an increase in the RLA, the latter of which occurs as a result of increased physiologic demand related to animal growth.

Figure 15:
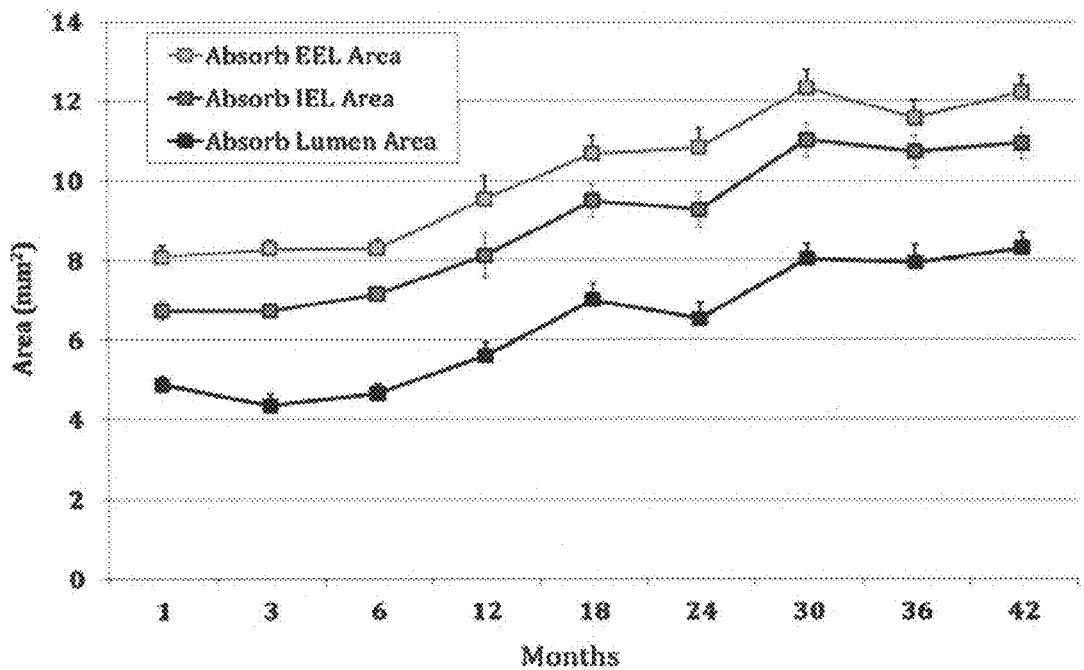
FIG. 15 depicts lumen area and areas within the external elastic lamina (EEL) and internal elastic lamina (IEL) of Absorb implanted arteries from 1 to 42 months.

FIG. 15 depicts lumen area and areas within the external elastic lamina (EEL) and internal elastic lamina (IEL) of Absorb implanted arteries from 1 to 42 months. After 6 months, progressive and coordinated increase in LA, EEL, and IEL are observed through 42 months.

By both IVUS and histomorphometry, Absorb implanted arteries demonstrate an increase in mean LA beginning around 12 months that progresses through 42 months, as shown in FIGS. 14 and 15, respectively. This LA increase is coordinated with an increase in the reference vessel lumen area (RLA) by IVUS and histomorphometrically with expansion in the areas within the EEL and IEL.

Figure 16:
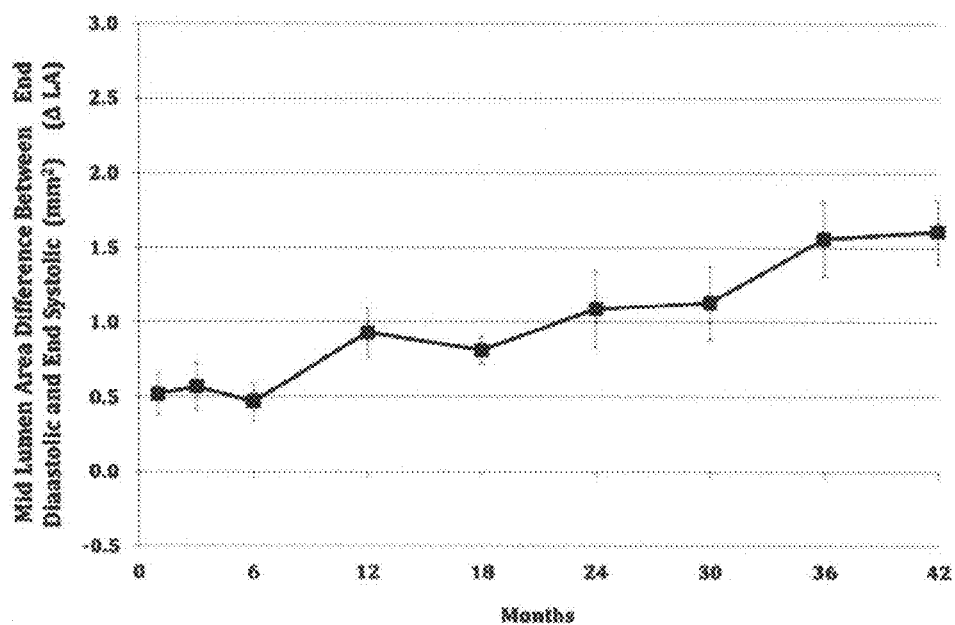
FIG. 16 depicts the absolute difference between end-diastolic and end-systolic mid scaffold lumen area (ΔLA) in Absorb implanted porcine coronary arteries from 1 to 42 months.

FIG. 16 depicts the absolute difference between end-diastolic and end-systolic mid scaffold lumen area (ΔLA) in Absorb implanted porcine coronary arteries from 1 to 42 months. Absorb implanted arteries demonstrate a continuous increase in ΔLA indicating a progressive return of pulsatility in the implanted region. In addition to lumen expansion, as illustrated with IVUS, in-scaffold pulsatility, as determined by the difference in areas at end-diastole and end-systole, also progressively increased from 12 to 42 months.

Figure 17:
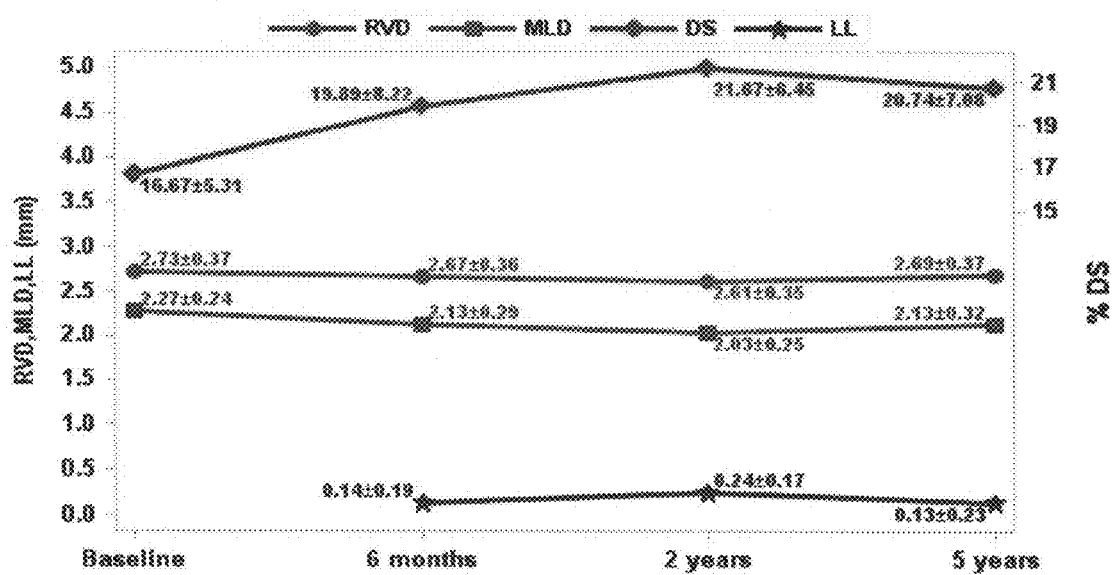
FIG. 17 depicts matched reference vessel diameter (RVD), minimum lumen diameter (MLD), late loss (LL) and percentage diameter stenosis (% DS) at baseline, 6-month, 2-year and 5-year follow-up.
Figure 18A:
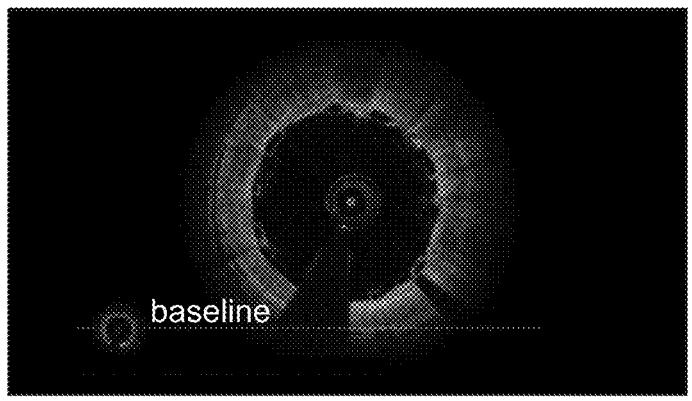
FIGS. 18A-D depicts OCT images of an artery treated with a bioabsorbable scaffold obtained post procedure, at baseline, 6 months, 2 years and 5 years, respectively.
Figure 18B:
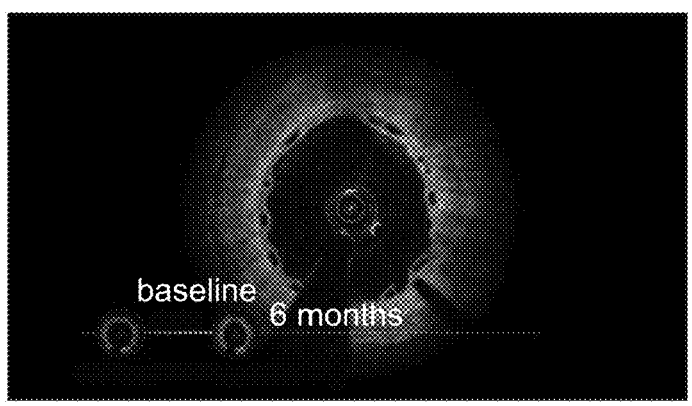
Figure 18C:
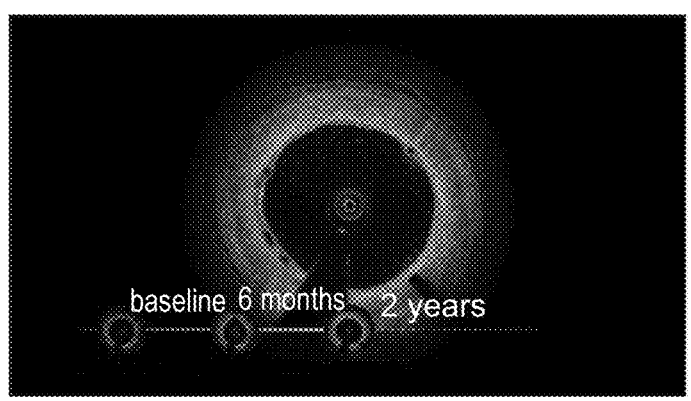
Figure 18D:
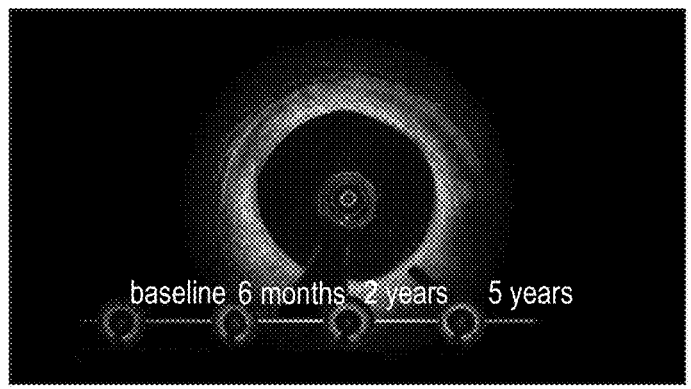

FIG. 17 depicts matched reference vessel diameter (RVD), minimum lumen diameter (MLD), late loss (LL) and percentage diameter stenosis (% DS) at baseline, 6-month, 2-year and 5-year follow-up. Based on the late loss results, 25% of patients showed a late gain at 5 years. The MLD is stable to 5 years. FIGS. 18A-D depicts OCT images of an artery treated with a bioabsorbable scaffold obtained post procedure, at baseline, 6 months, 2 years and 5 years, respectively. The black boxes near the outer interior edge of the images show the presence of struts at 6 months, 1 year, and 2 years. The number of struts shown decreases with time, indicating bioresorption. No struts are shown at 5 years, indicating complete bioresorption of the scaffold.

The four images correspond to three stages of the healing process associated with treatment with a bioresorbable scaffold disclosed herein. Between baseline and about 6 months, there is restoration of blood or coronary flow through the treated artery. Between about 6 months and about 12 months, the scaffold becomes structurally discontinuous and there is unconstrained vessel healing. Between about 1 year and 5 years and beyond, there is a reduction in late events driven by restored vascular function and improved coronary flow. The restored vascular function provides benefits such as lumen gain, plaque regression, and vasomotion.

After 12 months of degradation, the progressive decline in Mn contributes to a decline in radial strength, thus allowing for the in vivo observations of lumen gain and restoration of pulsatility. These results correlate to the clinical setting in which vasomotion and lumen gain have been demonstrated at 12 months in the Absorb clinical trial. (Ormiston J, Serruys P, et al. Circ Cardiovasc Interv 5:620-632, 2012; Serruys P, Ormiston J, et al. The Lancet 373:897-910, 2009; Serruys P, Onuma Y, et al. J Am Coll Cardiol 58:1578-88, 2011.)

After resorption, the polymer is progressively replaced by de novo formation of malleable provisional matrix such as proteoglycan. Despite its malleable and deformable structure the scaffold did not undergo any reduction in area. Following the coverage of struts and loss of mechanical support, it is assumed that the vessel can respond to medication which reduces the plaque burden without creating any malapposition, since the malleable and dismantling scaffold will follow the adaptive glagovian remodeling of the vessel wall.

A plaque burden reducing medication may be administered to reduce the plaque burden between the malleable scaffold and the vessel media. The plaque burden reducing medication may be administered after or only after the struts are covered by a neointimal layer. The plaque burden reducing medication may be administered after or only after outward compensatory enlargement of the vessel size starts. This prevents malapposition between the malleable scaffold and the vessel media due to outward displacement of the malleable scaffold as the vessel enlarges. The malleable scaffold will move outward with the vessel media and external elastic membrane (EEM), thus preventing malapposition.

The compensatory enlargement may starts at 1 year or about 1 year after deployment of the scaffold. The plaque burden reducing agent may be a statin. Representative statins include, but are not limited to, rosuvastatin, atorvastatin, fluvastatin, and lovastatin. A discussion of glagovian remodeling is in Journal of the American College of Cardiology, Schoenhagen, P, et al., J. of the American College of Cardiology, vol. 38, No. 2, 2001 (Appendix C). Adaptive glagovian remodeling refers to early plaque accumulation in human coronary arteries associated with compensatory enlargement of vessel size (positive remodeling). Therefore, lumen or luminal size is initially not affected by plaque growth. These complex changes of lumen, plaque, and external elastic membrane (EEM) may also affect plaque regression. In vivo studies of human coronary arteries using intravascular ultrasound (IVUS) imaging found a correlation between atheroma and external elastic membrane area. "Positive remodeling" as observed by Glagov et al. (Atherosclerosis 1997; 131 (Suppl.): S13-S14) describes an expansion in EEM area and "negative remodeling" describes shrinkage of EEM area at the lesion site.

Optical coherence tomography (OCT) has provided the investigators with an extraordinary imaging tool capable of scrutinizing micro-discontinuity of struts, but this optical technique cannot differentiate the polylactide from proteoglycan which is one of the first structural changes to occur in vascular reconstruction. However, the technique can precisely quantify, in microns, the thickness of the tissue layers that isolate the underlying plaque from the lumen. In contrast, ultrasonic interrogation of the polymeric strut can monitor the bioresorption process. Palpography, using radiofrequency backscattering has been able to analyze the subtle changes in vascular strain in great detail and can detect the return of the physiological cyclic strain.

It is expected that treatment with a BVS can result in late lumen enlargement, associated with wall thinning and adaptive remodeling.

The Absorb BVS device was tested in 101 patients of the ABSORB Cohort B study which was subdivided in two subgroups of patients: the first group (B1) underwent invasive imaging with QCA, IVUS gray scale, IVUS-VH and OCT at 6 and 24 months whereas the second group (B2) reported in detail in the current application underwent invasive imaging at 12 months and at 36 months.

Figure 2A:
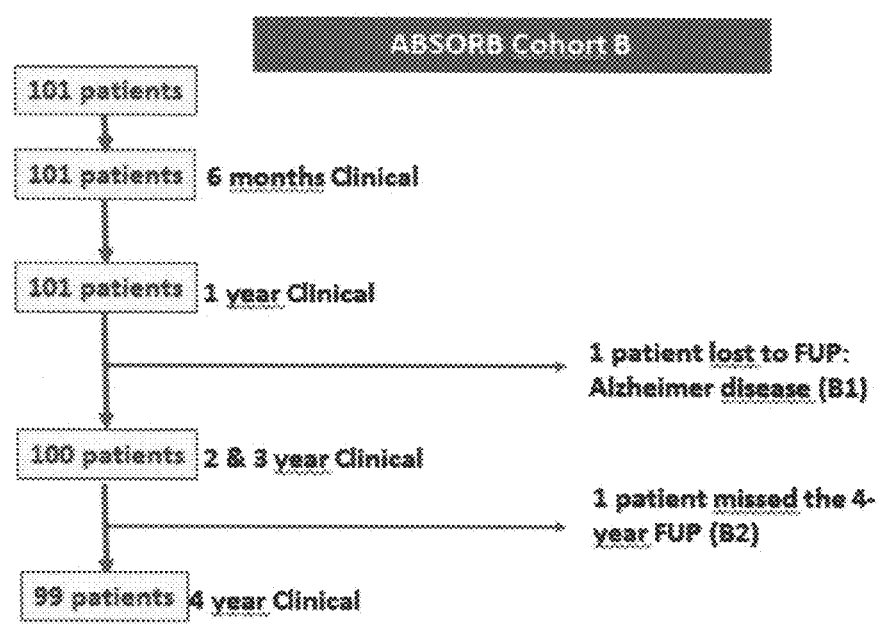
FIG. 2A depicts the overall patient inclusion of Cohort B.
Figure 2B:
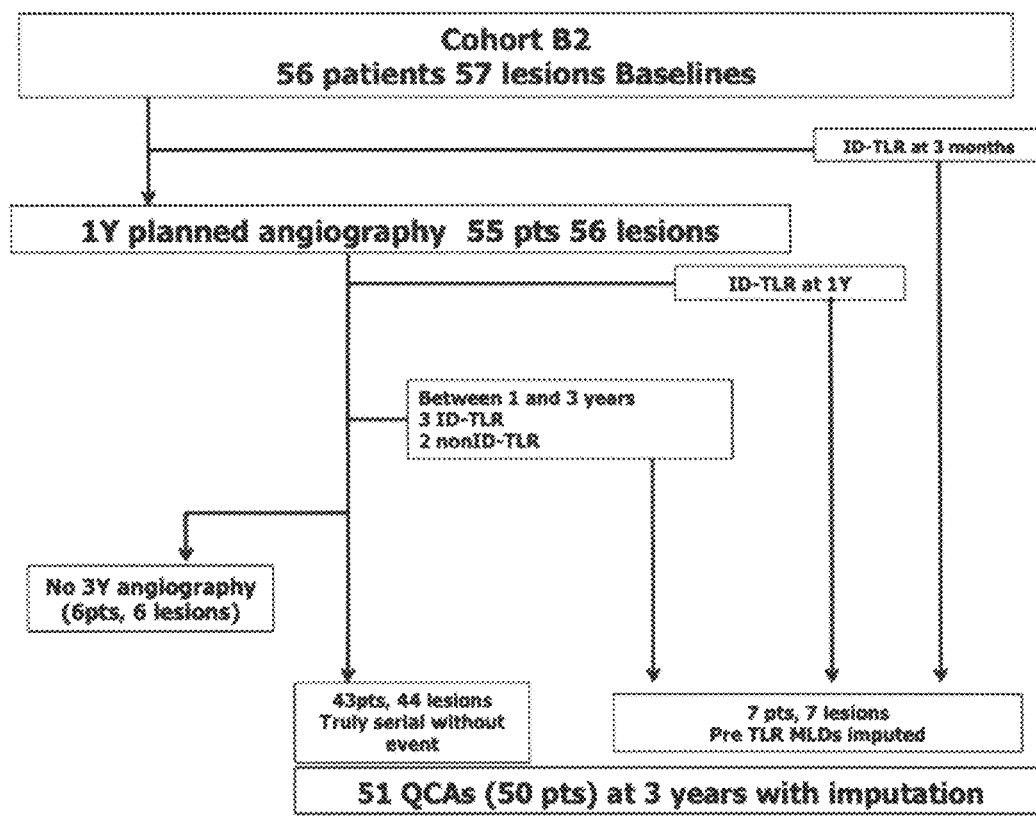
FIG. 2B depicts the patient flow chart of Cohort B2.

FIG. 2A depicts the overall patient inclusion of Cohort B. FIG. 2B depicts the patient flow chart of Cohort B2. The present application report describes the multimodality imaging performed post procedure, at 6, 12, 24 and 36 months and to report the clinical follow-up at 36 months of the entire patient cohort.

Figure 5A:
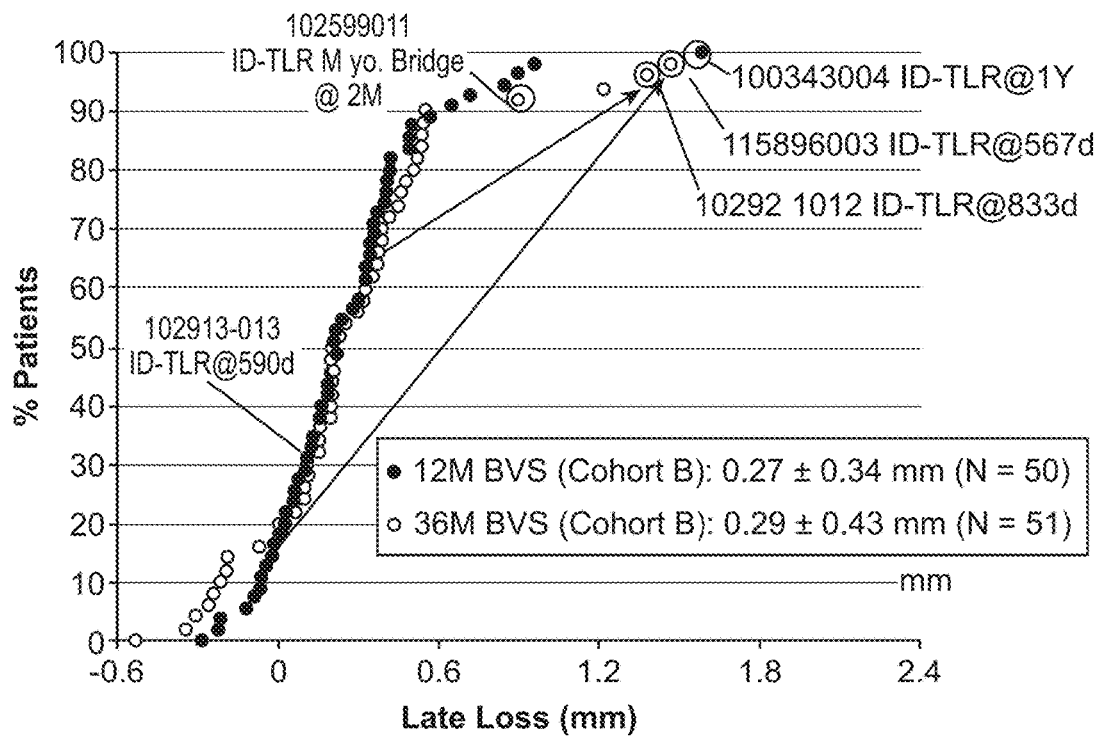
FIG. 5A depicts cumulative frequency distribution curves of angiographic late loss at 1 (light symbols) and 3 years (dark symbols) including QCA values at the time of target lesion revascularization whenever it occurs.
Figure 5B:
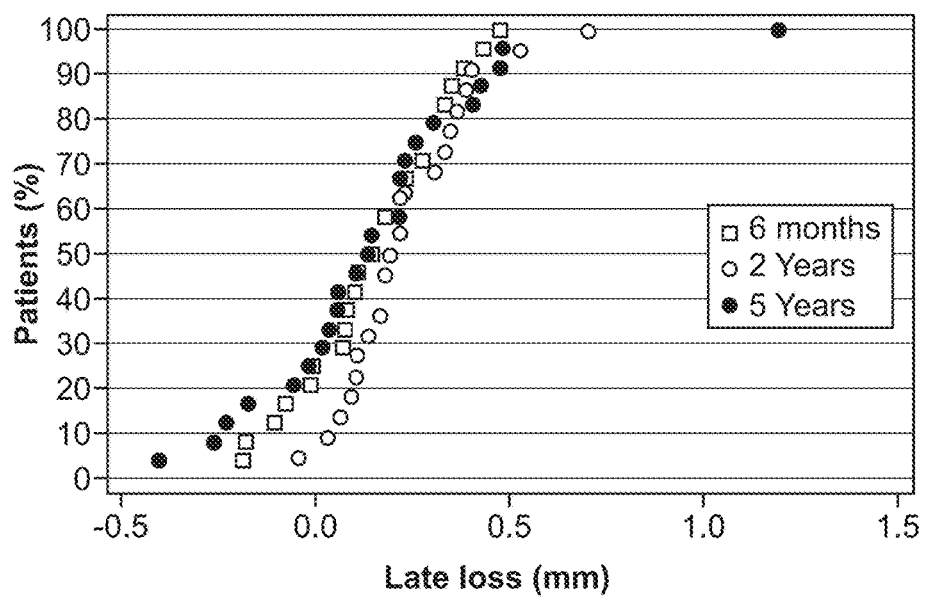
FIG. 5B depicts cumulative frequency distribution curves of angiographic late loss at 6 months, 2 years, and 5 years including QCA values at the time of target lesion revascularization whenever it occurs.

US 2010/0198330 discloses the clinical results for the first generation scaffold. US 2010/0198330 describes and illustrates in FIGS. 5A-C a schematic representation of exemplary time dependent behavior of a bioabsorbable stent after intervention at an afflicted section of a vessel. In addition, FIGS. 5A-C also show expected biological responses of the vessel to the stent as a function of time. The time scale shown is exemplary so the time dependence of stent behavior is a qualitative representation of the behavior the bioabsorbable stent of the present invention which elicits healing of the afflicted section. Each of FIGS. 5A-C shows the time dependence of the stent properties, the radial strength, drug release, mechanical integrity, and erosion or mass loss.

Definitions of vessel characteristics can be found in US 2010/0198330. Post-procedural or post-percutaneous coronary intervention (PCI) refers to a time point immediately after or almost immediately after stent deployment. "In stent" refers to a stented segment of a vessel. "Reference vessel diameter" (RVD) is the diameter of a vessel in areas adjacent to a diseased section of a vessel that appear either normal or only minimally diseased. "Minimal lumen diameter" (MLD) is the diameter of a diseased section of a vessel at the site of maximal reduction in the diameter. % "Diameter restenosis" (% DS) is the percent difference between the reference vessel diameter and the minimal lumen diameter: (RVD-MLD)/RVD. "Acute gain" is defined as the difference between pre- and postprocedural minimal lumen diameter. "Late loss" is defined as the difference between minimal luminal diameter after the procedure or post-percutaneous coronary intervention (PCI) and minimal luminal diameter at follow-up. "Pre-stenting" or "pre-implantation" refers to before implantation or deployment of the stent at a section of a blood vessel. "Post-stenting" or "post-implantation" refers to a time shortly after implantation or deployment of the stent at a section of a blood vessel. Measurements designated postimplantation are made, for example, immediately after a stent is implanted in a patient or the same day of implantation.

Angiographic assessment, vasomotion test, IVUS greyscale analysis, and IVUS based radiofrequency backscattering were analyzed by the independent core lab.

The Absorb BVS includes of a polymer backbone of Poly(L lactide) (PLLA) coated with a thin layer of a 1:1 mixture of Poly(D, L-lactide) (PDLLA) polymer, and the anti-proliferative drug everolimus to form an amorphous drug eluting coating matrix containing 100 micrograms of everolimus/$cm^2$ of scaffold. The scaffold structure has in-phase zigzag hoops linked by bridges that allow a highly uniform strut distribution, reduces maximum circular unsupported surface area and provides more uniform vessel wall support and drug transfer. Compared to the first generation of the scaffold, a modified manufacturing process eliminated impurities such as monomer, oligomer and solvents, which resulted in a slower hydrolysis (in vivo degradation) rate of the polymer, thus preserving its mechanical integrity for a longer period of time. The actual duration of resorption of the second generation is in vivo approximately 18 months longer than the first generation, and the mass loss of the second generation ABSORB scaffold takes approximately 36 months.

In each patient, the treated segment and the peri-scaffold segments (defined by a length of 5 mm, proximal and distal to the scaffold edge) were analyzed by quantitative coronary angiography (QCA) post-procedure and at follow-up using an interpolated method for the reference vessel diameter (RVD).

Changes in vasomotion (mean lumen diameter) prior to, and post nitrate were assessed in paired matched angiographic view(s) in the scaffolded segment and in the 5 mm proximal and 5 mm distal adjacent segments.

Treated vessels post-procedure and at follow-up were examined with phased array intravascular ultrasound catheters (EagleEye™; Volcano Corporation, Rancho Cordova, Calif.) using a pullback speed of 0.5 mm per second. The region of interest beginning 5 mm distal to and extending 5 mm proximal to the treated segment was examined. There are three contours that can be delineated by IVUS: the endoluminal contour (lumen area), the leading edge of the struts (scaffold area) and the EEM area (vessel area). There are thus four compartments that can be quantified in IVUS; the luminal area, the neointimal area between the lumen and the scaffold contours (=scaffold area-lumen area), the plaque behind the struts area (=vessel area—scaffold area) and the vessel area. Incomplete apposition was defined as one or more scaffold struts separated from the vessel wall, while acquired late incomplete apposition was defined as incomplete apposition at follow-up that was not present post-procedure. For echogenicity assessment of polymeric struts at baseline and follow-up, a computer-aided grayscale value analysis program for strut characterization was used.

Backscattering of radiofrequency signals provides information on vessel wall tissue composition (IVUS-VH). Four tissue components (necrotic core [NC]—red; dense calcium [DC]-white; fibrous [F]—green; and fibrofatty[FF]—light green) were identified with autoregressive classification systems, and expressed as percentages (per cross section, NC+DC+FF+F=100%). The change in quantitative analyses of these areas between implantation and follow-up was used as a surrogate assessment of the chemical and structural alteration of the polymeric struts.

Intravascular OCT imaging using either a time domain OCT (M3 system, LightLab Imaging (LLI), Westford, Mass.,) or a frequency domain OCT (C7XR system, LLI) was performed at baseline and at follow-up. None of the OCT acquisition was performed with an occlusion technique. The OCT measurements were performed either at 1 mm longitudinal intervals or at 200 micron intervals (strut core analysis) within the treated segment, using proprietary software for offline analysis (LLI).

The thickness of the coverage was measured between the endoluminal side of the strut core and the boundary of the lumen drawing the line of measurement from the mid part of the endoluminal edge of the black core of the struts toward the center of gravity of the lumen in the analyzed cross section. The threshold for the coverage is 30 microns which corresponds to the average inter-observer measurement (300 struts analyzed two times, 35±6 μm), of the endoluminal light backscattering frame of the strut. At 3 years, the appearance of the struts can be detected as a black core which sometimes displays irregular high-intensity areas, possibly indicative of the presence of de novo connective tissue (cellularization) that progressively replaces the proteoglycan that is initially present after the resorption of the polymer.

For binary variables, percentages were calculated. Continuous variables are presented as mean and standard deviation. Overall comparison was assessed by applying Friedman test and pairwise comparisons between post procedure and follow-up were performed by a Wilcoxon's signed rank test adjusted by Bonferroni method. As no formal hypothesis testing was planned for assessing the success of the study, no statistical adjustment was applied. P-values presented are exploratory analyses only and should therefore be interpreted cautiously. For imaging assessment, serial analysis including pre-TLR assessment is presented in the tables, while truly serial analysis of each time point excluding pre-TLR values is presented in the supplement.

Table 2 depicts the Baseline characteristics and Acute Success for the Cohort B clinical trial. In total 101 patients were enrolled in this study and the same investigational device (Absorb BVS first generation) was successfully implanted in all patients. Additional metallic drug-eluting stents were implanted in 3 lesions. Clinical follow-up at 3 years was available in all but one patient who withdrew consent, although the vital status of the patient was available through the referring physician. During the 3-year follow-up period, there were no possible, probable, or definite scaffold thrombosis. In summary, there were 3 non-Q-wave myocardial infarctions and 7 ID-TLRs, which resulted in a 3-year Major Adverse Cardiac Event rate of 10% (table 3). Dual antiplatelet therapy was maintained in 98% (99/101), 81.2% (82/101), 24.0% (24/101) and 21.6% (21/97) at 6, 12, 24, and 36 months respectively.

TABLE 2

Baseline characteristics and Acute Success.

|  | Total (n = 101) | Cohort B1 (n = 45) | Cohort B2 (n = 56) | p |
|---|---|---|---|---|
| Age (mean ± SD, years) | 62 ± 9 | 65 ± 9 | 60 ± 8 | 0.02 |
| Male gender (n (%)) | 73(72) | 33 (73) | 40 (71) | 0.83 |
| Current Smokers (n (%)) | 17(17) | 5 (11) | 12 (21) | 0.18 |
| Diabetes (n (%)) | 17(17) | 6 (13) | 11 (20) | 0.4 |
| Hypertension Requiring Medication (n (%)) | 62(62) | 27 (60) | 35 (64) | 0.71 |
| Hyperlipidemia Requiring Medication (n (%)) | 79(78) | 42 (93) | 37 (66) | 0.001 |
| Prior target vessel Intervention (n (%)) | 6(6) | 4 (9) | 2 (4) | 0.4 |
| Prior myocardial infarction (n (%)) | 25(25) | 16 (36) | 9 (16) | 0.03 |
| Target Vessel |  |  |  |  |
| Left Anterior Descending (n(%)) | 44(43) | 17 (38) | 27 (47) | 0.33 |
| Left Circumflex (n(%)) | 24(24) | 12 (27) | 12 (21) | — |
| Right Coronary Artery (n(%)) | 34(34) | 16 (36) | 18 (32) | 0.67 |
| AHA/ACC Lesion Classification |  |  |  |  |
| A (n(%)) | 1(1) | 1 (2) | 0 (0) | 0.44 |
| B1 (n(%)) | 55(55) | 20 (45) | 35 (63) | 0.09 |
| B2 (n(%)) | 40(40) | 22 (50) | 18 (32) | 0.07 |
| C (n(%)) | 4(4) | 1 (2) | 3 (5) | 0.63 |
| Acute Success |  |  |  |  |
| Clinical Device success (%) | 100 |  |  |  |
| Clinical Procedure (%) | 98 |  |  |  |
| Mean Reference Vessel Diameter (mm) | 2.61 ± 0.37 | 2.65 ± 0.46 | 2.58 ± 0.29 | 0.37 |
| Minimum Luminal Diameter (mm) | 1.06 ± 0.28 | 1.06 ± 0.32 | 1.06 ± 0.23 | 0.91 |
| Diameter Stenosis (%) | 59 ± 10 | 60 ± 12 | 59 ± 9 | 0.59 |
| Lesion Length (mm) | 9.9 ± 3.6 | 10.2 ± 3.9 | 9.7 ± 3.4 | 0.44 |

Clinical Device Success = successful delivery & deployment of the scaffold at intended target lesion & successful withdrawal of the scaffold delivery system w/attainment of final residual stenosis of less than 50% of the target lesion by QCA (by visual estimation if QCA unavailable). Standard pre-dilation catheters & post-dilatation catheters (if applicable) may be used. Bailout patients included as device success only if the above criteria for clinical device are met.
Clinical Procedure Success = same as definition above and/or using any adjunctive device without occurrence of ischemia driven major adverse cardiac event (MACE) during the hospital stay w/a maximum of first seven days post index procedure.

TABLE 3

Non-hierarchical count of clinical events over 4 years in the entire cohort B (n = 101).

|  | 30 days N = 101 | 6 months N = 101 | 12 months N = 101 | 24 months N = 100* | 3 years N = 100* | 4 years N = 99* |
|---|---|---|---|---|---|---|
| Cardiac death | 0 | 0 | 0 | 0 | 0 | 0 |
| Myocardial infarction, % (n) | 2.0 (2) | 3.0 (3) | 3.0 (3) | 3.0 (3) | 3.0 (3) | 3.0 (3) |
| Q-wave MI | 0 | 0 | 0 | 0 | 0 | 0 |
| non Q-wave MI, % (n) | 2.0 (2) | 3.0 (3) | 3.0 (3) | 3.0 (3) | 3.0 (3) | 3.0 (3) |
| Ischemia driven TLR, % (n) | 0 | 2.0 (2) | 4.0 (4) | 6.0 (6) | 7.0 (7) | 7.1 (7) |
| CABG | 0 | 0 | 0 | 0 | 0 | 0 |
| PCI, % (n) | 0 | 2.0 (2) | 4.0 (4) | 6.0 (6) | 7.0 (7) | 7.1 (7) |

TABLE 3-continued

Non-hierarchical count of clinical events over 4 years in the entire cohort B (n = 101).

|  | 30 days<br>N = 101 | 6 months<br>N = 101 | 12 months<br>N = 101 | 24 months<br>N = 100* | 3 years<br>N = 100* | 4 years<br>N = 99* |
|---|---|---|---|---|---|---|
| MACE, % (n) | 2.0 (2) | 5.0 (5) | 6.9 (7) | 9.0 (9) | 10.0 (10) | 10.1 (10) |
| TVF, % (n) | 2.0 (2) | 5.0 (5) | 6.9 (7) | 11.0 (11) | 13.0 (13) | 13.1 (13) |

*One patient lost to FU at 2-year FUP
*One patient missed the 4-year FUP
No Scaffold Thrombosis by ARC or Protocol
MI = Myocardial infarction,
TLR = Target lesion revascularization,
CABG = coronary artery bypass graft,
PCI = percutaneous coronary intervention,
MACE = Major adverse cardiac event,
TVF = Target vessel failure Table 4 depicts DAPT usage in the Absorb Cohort B trial.

TABLE 4

DAPT usage in the Absorb Cohort B trial.

|  | ABSORB Cohort B<br>n = 101 |
|---|---|
| Aspirin |  |
| At 3 years | 97.9% |
| At 4 years | 94.6% |
| Clopidogrel or Ticlopidine |  |
| At 3 years | 14.4% |
| At 4 years | 7.6% |
| DAPT Usage |  |
| At 3 years | 13.4% |
| At 4 years | 6.5% |

Table 5 shows the Baseline demographics of Absorb Cohort B patients compared with patients treated with a single 3.0×18 mm metallic Xience V. Table 6 shows the Baseline lesion characteristics of Absorb Cohort B patients vs. patients treated with a single 3.0×18 mm metallic Xience V.

TABLE 5

Baseline demographics of Absorb Cohort B patients vs. patients treated with a single 3.0 × 18 mm metallic Xience V.

|  | ABSORB Cohort B<br>n = 101 | XV (SPI + SPII + SPIII RCT)<br>n = 227 |
|---|---|---|
| Male (%) | 72 | 64 |
| Mean age (years) | 62 | 64 |
| Previous MI (%) | 25 | 23 |
| Diabetes mellitus (%) | 17 | 26 |
| Hypercholesterolemia req. med (%) | 78 | 73 |
| Hypertension req. med (%) | 62 | 74* |
| Current smoker (%) | 17 | 25 |

*p = 0.05

TABLE 6

Baseline lesion characteristics of Absorb Cohort B patients vs. patients treated with a single 3.0 × 18 mm metallic Xience V.

|  | ABSORB Cohort B<br>n = 101<br>$N_{lesions}$ = 102 | XV (SPI + SPII + SPIII RCT) n = 227<br>$N_{lesions}$ = 227 |
|---|---|---|
| Location of lesion (%) |  |  |
| LAD | 43 | 55 |
| RCA | 33 | 21* |
| LCX | 23 | 25 |
| Ramus | 1 | 0 |
| Lesion Classification (%) |  |  |
| A | 1 | 5 |
| B1 | 55 | 45 |
| B2 | 40 | 47 |
| C | 4 | 3 |

*p = 0.02

Between one and three years, 3 ischemia-driven (ID) target lesion revascularizations (TLR) and 2 non-ID TLR events occurred (FIG. 2B). The first patient received a 3.0×18 mm Absorb BVS in a large proximal LAD with a maximal diameter of 3.9 mm, resulting in 270-degrees of malapposition post procedure. The one-year angiographic follow-up showed no restenosis in the scaffolded segment while OCT demonstrated extensive malapposition. The patient presented with Braunwald Class I unstable angina on day 564. Repeat angiography on day 567 revealed a significant in-scaffold restenosis and the patient received a 3.0×18 mm Xience V stent. The 3-year angiography revealed no restenosis in this metallic drug-eluting stent. The second patient had recurrent stable angina (CCS Class II) with reversible anterior ischemia on myocardial scintigraphy. Follow-up coronary angiography at day 833 revealed a restenosis (% DS: 64%) of the scaffold in the mid LAD, which was treated with a 3.0×23 mm Xience V stent. The third patient, who had received a 3.0×18 mm Absorb BVS scaffold in the proximal RCA, underwent one-year planned angiography that revealed a progression of coronary stenoses in the distal RCA and the distal LM (102913-013). The patient underwent CABG on day 439 but presented with unstable angina on day 590. Repeat angiography demonstrated a significant new lesion (% DS: 74%) in the mid RCA proximal and distal to the anastomosis of a coronary bypass, including the distal bifurcation. Despite the absence of restenosis in the Absorb BVS scaffold (in-segment late loss 0.02 mm, in-scaffold late loss 0.12 mm), a 4.0×38 mm Promus Element stent was placed across the new lesion in the mid RCA with a short overlap of the Absorb BVS scaffold. Because of the overlap, the event was adjudicated by the independent clinical event committee as ID-TLR, although the ARC definitions of TLR pertain specifically to repeat procedures due to restenosis of the device or its adjacent segments 5 mm proximal and distal to the device.

One patient underwent a non-ID TLR at 2 years due to persistent incomplete strut apposition observed on OCT without any evidence of ischemia. The other patient (102913-012) had a non-ID TLR in the proximal LAD at day 722 to treat a new stenosis in the left main trunk without binary restenosis in the Absorb BVS scaffold (in-scaffold LL: 0.55 mm, in-segment LL: 0.38 mm). During the process of stent implantation in the left main stem, the scaffolded lesion was dilated by a balloon and therefore the event was adjudicated as non-ID TLR despite absence of binary restenosis in the scaffolded segment.

FIG. 3A depicts graphical illustration of the measurements of QCA without pre total lesion revascularization (TLR) value performed post procedure at 6, 12, 24 and 36 months. FIG. 3B depicts the measurements of QCA with pre TLR performed post procedure at 6, 12, 24 and 36 months. FIG. 3C depicts graphical illustration of the measurements of IVUS performed post procedure at 6, 12, 24 and 36 months. FIG. 3D depicts graphical illustration of the measurements of OCT performed post procedure at 6, 12, 24 and 36 months FIGS. 3A-B show the late loss at 6, 12, 24 and 36 months was 0.19, 0.27, 0.27 and 0.29 mm, respectively. In the group without TLR, the average late loss was similar at 1 year (0.22 mm) and 3 years (0.20 mm). For the entire cohort (n=101), there were 6 in-segment restenosis at 3 years with a binary restenosis rate of 6%.

In table 7, the angiographic results of 1 to 4 year follow-up including pre-TLR values are presented. Among the 5 cases with TLR between 1 year and 3 years, 3 were clinically driven while 2 were not. Among the 3 clinically driven TLR, 2 presented with a binary restenosis in the scaffolded segment.

TABLE 7

Results of quantitative angiographic analysis (QCA) in cohort B2 carrying forward the last QCA observation prior to the inter-current target lesion revascularization.

| | Proximal | In-scaffold | Distal |
|---|---|---|---|
| MLD (mm) | | | |
| Post procedure | 2.44 ± 0.37 (45) | 2.27 ± 0.23 (51) | 2.17 ± 0.36 (50) |
| At 1 year | 2.34 ± 0.38 (45) | 2.01 ± 0.34 (51) | 2.10 ± 0.32 (50) |
| At 3 years | 2.31 ± 0.42 (45) | 1.96 ± 0.45 (51) | 2.05 ± 0.37 (50) |
| P value (post-1 Y) | 0.0440 | <.0001 | 0.1033 |
| P value (post-3 Y) | 0.0213 | <.0001 | 0.0621 |
| P value (1 Y-3 Y) | 0.8170 | 0.4613 | 0.6631 |
| Late Loss 1 Y, mm | 0.10 ± 0.30 (43) | 0.27 ± 0.34 (50) | 0.07 ± 0.27 (49) |
| Late Loss 3 Y, mm | 0.14 ± 0.31 (44) | 0.29 ± 0.43 (51) | 0.08 ± 0.37 (49) |
| P value (1 Y-3 Y) | 0.2591 | 1.0000 | 0.7634 |
| Diameter Stenosis, % | | | |
| Post procedure | 13.1 ± 8.6 (45) | 14.9 ± 5.3 (51) | 15.2 ± 9.7 (50) |
| At 1 year | 12.1 ± 12.0 (45) | 21.1 ± 11.6 (51) | 13.7 ± 9.9 (50) |
| At 3 years | 13.1 ± 10.4 (45) | 23.2 ± 14.9 (51) | 16.1 ± 9.8 (50) |
| P value (post-1 Y) | 0.4578 | 0.0016 | 0.0981 |
| P value (post-3 Y) | 0.6986 | 0.0004 | 0.9502 |
| P value (1 Y-3 Y) | 0.7024 | 0.6131 | 0.2332 |
| Binary restenosis 3 Y | 0% (0/45) | 7.8% (4/51) | 2.0% (1/50) |
| RVD | | | |
| Post procedure | 2.81 ± 0.30 (45) | 2.67 ± 0.23 (51) | 2.56 ± 0.25 (50) |
| At 1 year | 2.67 ± 0.33 (45) | 2.56 ± 0.29 (51) | 2.44 ± 0.29 (50) |
| At 3 years | 2.67 ± 0.39 (45) | 2.57 ± 0.37 (51) | 2.45 ± 0.34 (50) |
| P value (post-1 Y) | 0.0006 | 0.0006 | <.0001 |
| P value (post-3 Y) | 0.0019 | 0.0031 | 0.0063 |
| P value (1 Y-3 Y) | 0.9858 | 0.7316 | 0.6204 |

MLD = minimum lumen diameter, RVD = reference vessel diameter

Figure 4A:
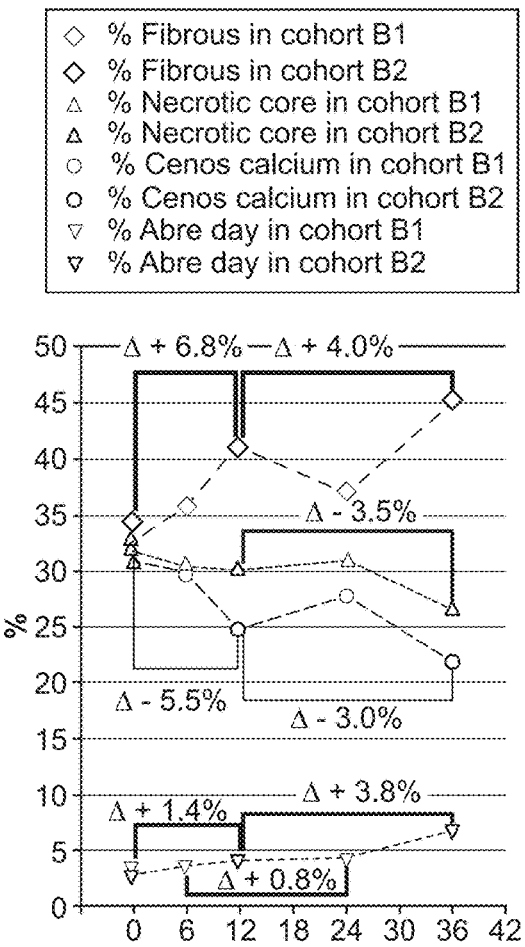
FIG. 4A depicts graphical illustration of the measurements in IVUS-VH performed post procedure, at 6, 12, 24 and 36 months.
Figure 4B:
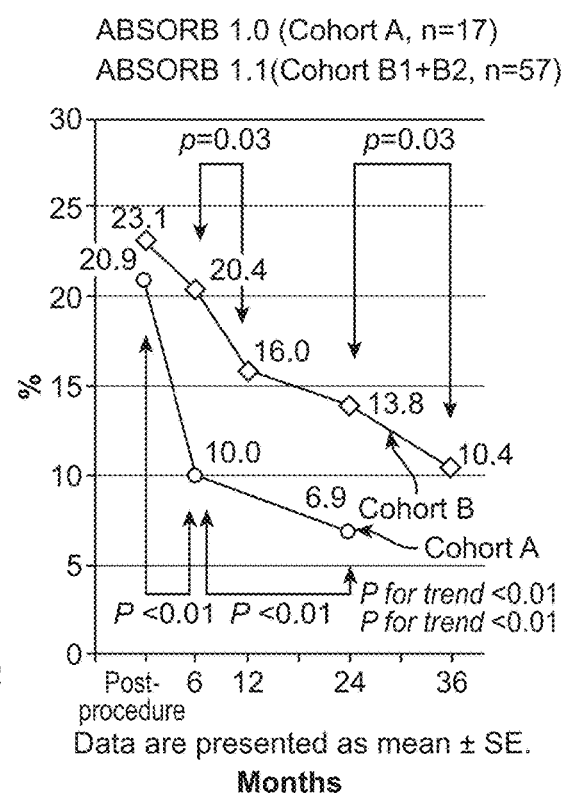
FIG. 4B depicts graphical illustration of the measurements in echogenicity performed post procedure at 6, 12, 24 and 36 months.

FIG. 4A depicts graphical illustration of the measurements in IVUS-VH performed post procedure at 6, 12, 24 and 36 months. FIG. 4B depicts graphical illustration of the measurements in echogenicity performed post procedure at 6, 12, 24 and 36 months. FIG. 4-B shows the changes in virtual histology over time, the polymeric struts are initially detected as pseudo dense calcium surrounded by necrotic core and interfere with the assessment of endogenous dense calcium and necrotic core. However, the sharp decrease in dense calcium and necrotic core between 24 and 36 months may also reflect the end of the inflammatory process with regression of the plaque behind the struts as illustrated in the FIG. 3C. The steady increase of fibrous and fibrofatty component may correspond to the neointimal formation.

The changes in % hyper-echogenicity are shown over time for the ABSORB Cohort B and Cohort A. For echogenicity assessment of the polymeric struts at baseline and follow-up, a computer-aided grayscale value analysis program for strut characterization was used.

Between 1 and 3 years there were no statistically significant differences in MLD, late loss, diameter stenosis and reference diameter in the patients with serial QCA data carrying forward the last observation at the time of TLR.

In 47 patients the mean lumen diameter inside the scaffold measured prior to and following intracoronary injection of nitrate showed a significant increase in the scaffold from 2.45±0.37 mm to 2.50±0.39 mm (p=0.005). FIGS. 3C-D shows the relative changes of mean LD in the proximal, distal, and scaffolded segment.

IVUS analysis is available post procedure and at 6 months, 1 year, 2 years, 3 years, and 5 years. FIG. 5A depicts cumulative frequency distribution curves of angiographic late loss at 1 (light symbols) and 3 years (dark symbols) including QCA values at the time of target lesion revascularization whenever it occurs. FIG. 5B depicts cumulative frequency distribution curves of angiographic late loss at 6 months, 2 years, and 5 years including QCA values at the time of target lesion revascularization whenever it occurs. The red arrows indicate the important changes in late loss between 1 and 3 years in patients who underwent ID-TLR (ischemia driven target lesion revascularization). As shown in Tables 8A and 8B, in the Cohort B2, serial IVUS analysis is available post procedure, at 12 and 36 months in 44 patients with 45 lesions, including 3 pre-TLR IVUS values. Table 9 summarizes the results of IVUS analysis in Tables 8A and 8B. Tables 8A and B. Gray-scale quantitative intravascular ultrasound carrying forward the last IVUS observation prior to the inter-current target lesion revascularization if available.

TABLE 8

Gray-scale quantitative intravascular ultrasound carrying forward the last IVUS observation prior to the inter-current target lesion revascularization if available.

| | BL | 1 Y | 3 Y | Difference BL-1 Y* | Difference 1 Y-3 Y* | Difference BL-3 Y* | P values BL-1 Y | P values 1 Y-3 Y | P values BL-3 Y | Friedman P-value |
|---|---|---|---|---|---|---|---|---|---|---|
| IVUS Grey-Scale | (n = 45) | (n = 45) | (n = 45) | 45 pairs | 45 pairs | 45 pairs | | | | |
| Mean Vessel area, $mm^2$ | 13.79 ± 2.37 | 14.43 ± 2.64 | 14.58 ± 2.67 | −0.64 ± 1.62 | −0.15 ± 1.09 | −0.79 ± 1.54 | 0.18 | 0.18 | 0.18 | 0.18 |
| Mean Scaffold area, $mm^2$ | 6.29 ± 0.91 | 6.35 ± 0.99 | 7.08 ± 1.55 | −0.06 ± 0.59 | −0.73 ± 0.90 | −0.80 ± 1.26 | n.s. | <0.001 | <0.001 | <0.001 |
| Min Scaffold area, $mm^2$ | 5.08 ± 0.90 | 5.09 ± 0.90 | 5.33 ± 1.21 | −0.00 ± 0.63 | −0.25 ± 0.73 | −0.25 ± 1.03 | 0.11 | 0.11 | 0.11 | 0.11 |
| Neointimal hyperplasia area, $mm^2$ | | 0.08 ± 0.13 | 0.28 ± 0.41 | | −0.20 ± 0.41 | | | 0.0017 | | 0.007 |
| Minimum lumen area, $mm^2$ | 5.08 ± 0.90 | 4.99 ± 0.94 | 5.08 ± 1.35 | 0.09 ± 0.72 | −0.09 ± 0.84 | 0.00 ± 1.14 | 0.62 | 9.62 | 0.62 | 0.62 |
| Mean Lumen Area, $mm^2$ | 6.29 ± 0.90 | 6.35 ± 1.17 | 6.81 ± 1.62 | −0.06 ± 0.88 | −0.46 ± 0.90 | −0.52 ± 1.32 | n.s. | 0.046 | 0.0017 | 0.0068 |
| Plaque behind strut, $mm^2$ | 7.50 ± 1.82 | 8.08 ± 2.03 | 7.49 ± 1.76 | −0.57 ± 1.29 | 0.58 ± 1.05 | 0.01 ± 0.69 | 0.0066 | n.s. | <0.0001 | 0.0057 |
| Total Plaque Area, $mm^2$ | 7.50 ± 1.82 | 8.08 ± 1.94 | 7.77 ± 1.73 | −0.58 ± 1.08 | 0.31 ± 0.93 | −0.27 ± 0.84 | 0.0006 | n.s. | 0.012 | 0.004 |
| Incomplete strut apposition, $mm^2$ | 1.17 ± 0.23 | 5.05 ± 0.52 | 1.05 ± 0.97 | | | | | | | |
| | N = 2 | N = 2 | N = 3 | | | | | | | |

TABLE 8B

| | P values BL-1Y | P values 1Y-3Y | P values BL-3Y | Friedman P-value |
|---|---|---|---|---|
| IVUS Grey-Scale | | | | |
| Mean Vessel area, $mm^2$ | 0.18 | 0.18 | 0.18 | 0.18 |
| Mean Scaffold area, $mm^2$ | n.s. | <0.001 | <0.001 | <0.001 |
| Min Scaffold area, $mm^2$ | 0.11 | 0.11 | 0.11 | 0.11 |
| Neointimal hyperplasia area, $mm^2$ | | 0.0017 | | 0.007 |
| Minimum lumen area, $mm^2$ | 0.62 | 9.62 | 0.62 | 0.62 |
| Mean Lumen Area, $mm^2$ | n.s. | 0.046 | 0.0017 | 0.0068 |
| Plaque behind strut, $mm^2$ | 0.0066 | n.s. | <0.0001 | 0.0057 |
| Total Plaque Area, $mm^2$ | 0.0006 | n.s. | 0.012 | 0.004 |
| Incomplete strut apposition, $mm^2$ | | | | |

TABLE 9

Summary of IVUS results in Table 8.

| Vessel Property | Change from BL to 1 Y | Change from 1 Y to 3 Y | Change from BL to 3 Y |
|---|---|---|---|
| Mean Vessel Area | Increase | Increase | Increase |
| Mean Scaffold Area | ~ unchanged | Increase | Increase |
| Min Scaffold Area | ~ unchanged | Increase | Increase |
| Neointimal Hyperplasia Area | — | Increase | — |
| Min Lumen Area | ~ unchanged | ~ unchanged | ~ unchanged |
| Mean Lumen Area | ~ unchanged | Increase | Increase |
| Plaque Behind Strut | Increase | Decrease | ~ unchanged |
| Total Plaque Area | Increase | Decrease | Increase |

In the overall analysis one of the most striking observations was a significant increase in mean scaffold, mean lumen, mean total plaque and mean vessel area between the first and the second year of observation, as shown in FIG. 5A. This enlargement of the scaffold accommodated for the modest increase in neointimal area at 2 years (0.25 mm$^2$) detected by ultrasound, so that the minimal lumen area remained unchanged at 12 and 24 months. Mean lumen area did increase between 12 and 24 months.

Between 2 years and 3 years there is significant plaque reduction with a small non-significant increase between post procedure and 3 years ($\Delta$+0.27 mm$^2$, p=0.08). The expansive remodeling in vessel area documented at 2 years regressed considerably at 3 years in parallel with the reduction in plaque behind the struts.

In patients with serial IVUS at one and 3 years, incomplete apposition was observed at 3 years in 3 patients with an average malapposed area of 1.05±0.97 mm$^2$. Two patients had malapposition at baseline, which resolved at 1 and 3 years. At one year, two patients developed late acquired malapposition, which was resolved at 3 years. Three patients, who had no malapposition at baseline and one year, developed malapposition at 3 years.

The results of echogenicity and VH analysis are presented in Tables 8A and 8B. Percent hyperechogenicity on greyscale radiofrequency backscattering from dense calcium and necrotic core substantially decreased between the second and third year, whereas fibrous and fibrofatty tissue significantly increased between the second and third year.

OCT results are shown in Tables 10A and 10B and the results are summarized in Table 11. After an initial decrease in minimal and mean lumen area, stabilization of these parameters was observed, despite an increase in neointima between one and 3 years, which was compensated by the parallel increase in mean and minimum scaffold area.

Tables 10A and 10B. Optical coherence tomography results carrying forward the last OCT observation prior to the inter-current target lesion revascularization if available.

TABLE 10

Optical coherence tomography results carrying forward the last OCT observation prior to the inter-current target lesion revascularization if available.

| | Post procedure | 12 month | 36 month | Difference BL-1 Y* | Difference 1 Y-3 Y* | Difference BL-3 Y* | P values BL-1 Y | P values 1 Y-3 Y | P values BL-3 Y | Friedman p-value |
|---|---|---|---|---|---|---|---|---|---|---|
| | (n = 19) | (n = 19) | (n = 19) | 19 pairs | 19 Pairs | 19 Pairs | | | | |
| Mean scaffold area, mm$^2$ | 7.76 ± 1.07 | 7.51 ± 0.95 | 8.64 ± 2.15 | 0.24 ± 0.62 | −0.88 ± 1.72 | −1.13 ± 1.42 | n.s. | 0.0024 | n.s. | 0.0155 |
| Min scaffold area, mm$^2$ | 6.29 ± 0.87 | 6.02 ± 0.98 | 6.69 ± 1.72 | 0.27 ± 0.88 | −0.67 ± 1.10 | −0.40 ± 1.63 | 0.32 | 0.32 | 0.32 | 0.32 |
| Mean black core area, mm$^2$ | 0.19 ± 0.03 | 0.16 ± 0.02 | 0.20 ± 0.03 | 0.03 ± 0.04 | −0.01 ± 0.04 | −0.04 ± 0.03 | 0.01 | 0.0001 | n.s. | 0.002 |
| Mean neointimal area, mm$^2$ | | 1.41 ± 0.68 | 2.35 ± 0.68 | | −0.93 ± 0.84 | | | <0.001 | | |
| Mean lumen area, mm$^2$ | 7.72 ± 1.17 | 6.01 ± 1.29 | 6.09 ± 1.67 | 1.71 ± 1.31 | −0.08 ± 0.86 | 1.63 ± 1.36 | 0.001 | n.s. | 0.0013 | <0.0001 |
| Min lumen area, mm$^2$ | 6.19 ± 0.96 | 4.43 ± 1.08 | 4.34 ± 1.48 | 1.76 ± 1.19 | 0.09 ± 0.93 | 1.84 ± 1.47 | <0.0001 | n.s. | <0.0001 | <0.0001 |
| Mean strut core volume*, mm$^3$ | 3.34 | 3.32 | 3.09 | −0.02 | −0.22 | −0.25 | 0.916 | 0.039 | 0.116 | |
| Uncovered strut. % | | 3.25 ± 2.86 | 1.73 ± 1.53 | | 1.52 ± 2.24 | | | 0.01 | | |
| Incomplete strut apposition | 0.27 ± 0.29 | 2.68 ± 1.63 | 0.60 ± 0.47 | | | | | | | |
| | (n = 16) | (n = 3) | (n = 3) | | | | | | | |

TABLE 10B

| | P values BL-1Y | P values 1Y-3Y | P values BL-3Y | Friedman p-value |
|---|---|---|---|---|
| Mean scaffold area, mm$^2$ | n.s. | 0.0024 | n.s. | 0.0155 |
| Min scaffold area, mm$^2$ | 0.32 | 0.32 | 0.32 | 0.32 |

TABLE 10B-continued

|  | P values BL-1Y | P values 1Y-3Y | P values BL-3Y | Friedman p-value |
|---|---|---|---|---|
| Mean black core area, mm$^2$ | 0.01 | 0.0001 | n.s. | 0.002 |
| Mean neointimal area, mm$^2$ |  | <0.001 |  |  |
| Mean lumen area, mm$^2$ | 0.001 | n.s. | 0.0013 | <0.0001 |
| Min lumen area, mm$^2$ | <0.0001 | n.s. | <0.0001 | <0.0001 |
| Mean strut core volume*, mm$^3$ | 0.916 | 0.039 | 0.116 |  |
| Uncovered strut, % |  | 0.01 |  |  |
| Incomplete strut apposition |  |  |  |  |

TABLE 11

Summary of OCT results.

| Property | Change from BL to 1 Y | Change from 1 Y to 3 Y | Change from BL to 3 Y |
|---|---|---|---|
| Mean scaffold area | Decrease | Increase | Increase |
| Min scaffold area | Decrease | Increase | Increase |
| Mean black core area | 0.03 ± 0.04 | −0.01 ± 0.04 | −0.04 ± 0.03 |
| Mean neointimal area | — | 0.93 ± 0.84 | — |
| Mean lumen area | Decrease | ~ unchanged | Decrease |
| Min lumen area | Decrease | ~ unchanged | Decrease |
| Mean strut core volume | ~ unchanged | Increase | Increase |
| Uncovered strut | — | Decrease | — |

At the time of the trial design, the OCT investigation was optional. In the Cohort B2, post procedure 20 patients with 21 lesions underwent an OCT. Out of these 21 lesions, 19 underwent serial OCT at one year and 3 years including two patients with OCT prior to TLR (electronic supplement). In the Cohort B2, OCT measurements demonstrated, between 1 and 3 years, a significant late scaffold area enlargement (mean: Δ1.13±1.42 mm$^2$, p<0.001, minimum: Δ0.67±1.10 mm$^2$, p=0.03) and a significant increase in neointimal formation (Δ0.94±0.84 mm$^2$, p<0.001) with as a result the mean and minimal lumen area remaining stable between the two follow-up time-points.

The number of struts counted in an all-frame analysis (200 micron interval) steadily increased from baseline (672.2±32.2), to one year (702.2±48.7) and to 3 years (726.4±70.1), probably reflecting the dismantling of the scaffold. The mean black core area was unchanged from baseline to 3 years. The contours of the black box were visually delineated by the analyst of the core lab (frame with one interval) resulting in an unchanged quantitative assessment of the area. In an all-frame analysis only available in 13 patients, the black core volume showed a modest but significant decrease from one to 3 years. Ninety-eight percent of struts were covered and three scaffolds showed malapposed struts with an average malapposition area of 0.60 mm$^2$.

The main findings of the results are the following: i) Echogenicity and VH analysis suggest advanced bioresorption of the polymeric device. ii) On IVUS, the mean and minimum scaffold area significantly increase and compensate for the increase in neointimal hyperplasia—resulting in an increase of mean lumen area from 1 to 3 years with an unchanged minimal lumen area from 1 year to 3 years. The total plaque area shows a biphasic change with a significant increase between the first and second year and a significant plaque reduction between the second and third year follow-up. iii) OCT confirms the IVUS findings regarding the increase in the scaffold area and neointimal area from 1 to 3 years; iv) Angiographic late luminal loss between 1 and 3 years remains unchanged; v) the major adverse cardiac events at 3 years remains low.

Data showed changes in % hyperechogenicity in serial pullbacks at 6 and 24 months and at 1 and 3 years. These two non-serial observations are combined with an identical ongoing bioresorption process that has not yet reached its minimal value compared to the bioresorption of the Cohort A device, using a first generation scaffold with a faster resorption. In the preclinical study, full resorption is complete at 36 months. The use of ultrasound to monitor the degradation process of biopolymers has been proposed previously and tested in an in vitro setup. Wu et al. showed that the degradation rate of biodegradable polymers can be closely monitored by ultrasound techniques.

At variance with this mode of investigation, OCT assessment of the black core volume showed a significant but modest decrease between one and 3 years. It is important to remember that this optical technique cannot differentiate the polylactide from provisional matrix such as proteoglycan and the preclinical studies have clearly demonstrated by gel permeation chromatography the absence of the polylactide at 3 years with its replacement by proteoglycan. In addition, the black core area was determined by visual contour delineation and does not take into account subtle change in greyness of black cores or the appearance of light reflecting structures inside the black core. (FIG. 7)

Figure 7:
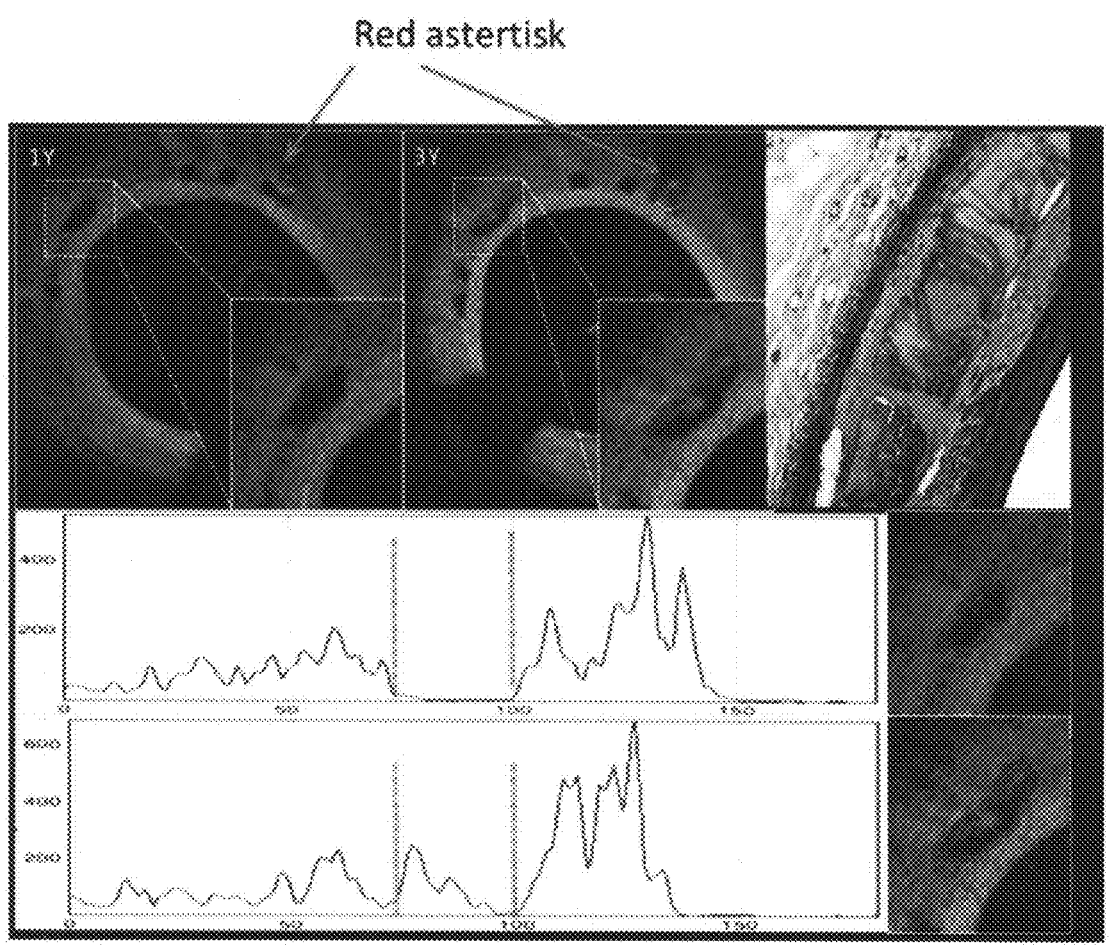
FIG. 7 depicts matched OCT cross-sections according to the presence of distal metallic markers (red asterisks) at 1 and 3 years.

FIG. 7 depicts matched OCT cross-sections according to the presence of distal metallic markers (red asterisks) at 1 and 3 years. One of the matched struts next to the marker (asterisk) was analyzed by light reflectivity. At 3 years, the strut core that was initially black became partially filled by a white nucleus exhibiting high light reflectivity. Tracings at the bottom showed graphically the light reflectivity along the scan line of incident light (red). The vertical green dotted lines correspond to the adluminal and abluminal boundaries of the black core either empty or partially occupied by white nucleus. Histological picture (Movat staining, 20x) of porcine coronary artery 36 months after implantation of ABSORB scaffold showed provisional matrix (glycoconjugates) in purple, filling the void previously occupied by the polymeric strut. A cellularized (black dots) area with connective tissue is located at the center of the strut void and is connected by peduncle to the subintima. Multi-layers of smooth muscle cells are overlying the strut voids. OCT images of the histological structures in porcine model are very similar to those observed in human. The light intensity was analyzed using an open source software.

Thus, it is possible that polylactide has been replaced by proteoglycan in these patients, but that change is undetectable by OCT. Assessment of light reflectivity should be applied to objectively assess subtle modifications of light absorption and back scattering. Previous preclinical assessments of histology and OCT have indicated that changes in strut appearance on OCT correspond to the cellularization of the provisional matrix and the appearance of connective tissues surrounding the cell nuclei stained in black in a Movat histological preparation (FIG. 7). Preclinical investigation of scaffolded porcine coronary artery models at 2, 3 and 4 years combining OCT and histology indicated that the next phase will involve a shrinkage and thinning of the neointimal tissue with a histological disappearance of strut footprints. This last integration process will result in late wall thinning with late lumen enlargement. Noteworthy, the persistence of black core at 3 years allows for the tracking of the outward displacement of individual struts and documentation of the increase in scaffold area that clearly occurs between 1 and 3 years. At 4 years, this OCT information will no longer be available since the OCT signal will no longer be visible.

Between 1 and 3 years, the OCT assessment documented an enlargement of the scaffold area (1.13 mm$^2$) in parallel with an increase in neointima between and on top of the struts (0.94 mm$^2$). The net result is on average an unchanged mean lumen area. (58% showed an increase between 1 and 3 years while 42% showed a decrease). It seems that, at 3 years, a kind of equilibrium inside the scaffold between the outward displacement of the scaffold and inward growth of neointimal tissue has been reached. The absence of late luminal loss between 1 and 3 years appears to be the net result of this equilibrium (FIGS. 3A-D and 4A-B).

As shown in FIG. 1B, between 1 and 3 years the radial strength decreases from about 1000 mm Hg (about 80% of the initial value) to about 50 mm Hg, about a 95% drop from the initial. The strut count increase between from baseline to 1 year and 1 year to 3 years reflects a dismantling or increased discontinuity of the scaffold in these time frames. Thus, it may be hypothesized that the scaffold enlargement may be correlated to the significant drop in radial strength, scaffold discontinuity, and growth of neointima. The neointima encapsulates the scaffold which has freedom radial movement due to the reduction in radial strength and discontinuity. Outward movement of the vessel wall is allowed by the scaffold. Thus, it may be advantageous for significant reduction in radial strength and/or discontinuities in the scaffold to develop in a time frame of neointimal growth over the scaffold.

The data regarding the time dependence of scaffold properties (molecular weight and radial strength) and the disclosed clinical data provides guidance in treating a coronary lesion, in particular, stabilizing lumen area of a scaffolded segment.

A method of stabilizing lumen area of a scaffolded segment of a coronary may include selecting or designing a bioabsorbable polymer scaffold having a reduction in radial strength and scaffold discontinuity during a particular time period post-deployment. The reduction in radial strength and scaffold discontinuity increases the malleability of the scaffold and results in enlargement of the vessel and scaffold area during the time period post-deployment of a bioabsorbable scaffold. The time period is selected to correspond to a time period of neointimal growth over the struts of the scaffold. The selected bioabsorbable scaffold is deployed at a stenotic segment of an artery of the patient which supports the segment for a period of time at an increased diameter to restore normal blood flow. However, the deployed scaffold restricts radial movement of the segment, thus preventing vasomotion and vessel enlargement. The lumen area is stabilized as the freedom of radial movement to the segment is restored due to onset of malleability of the scaffold as it degrades. As a result, the vessel and scaffold are enlarged during the time period. The enlarging of the vessel and scaffold (which tends to increase lumen size) compensates for the growth of neointima over the scaffold (which tends to decrease lumen size) during the time period which stabilizes the area of the lumen of the segment.

The scaffold may be designed to exhibit enlargement at any selected time by adjusting properties that contribute to onset of malleability. The malleability depends on the molecular weight, radial strength, and fracture toughness of the scaffold. The time period of the onset of malleability depends on the degradation rate of the scaffold polymer. These scaffold properties and thus the onset of malleability can be adjusted to obtain a selected time period for restoring freedom radial movement, and thus enlargement of the vessel and scaffold. The adjusting can be performed through selection of scaffold material and adjustment of properties such as crystallinity and biaxial orientation by modulating processing techniques, as described in US 2010/0198330, US 2011/0021717, and US 2012/0290070. For example, the degradation rate can be adjusted by the changing the amount of monomer concentration in the scaffold polymer through selection of a resin material, extrusion processing conditions, or both.

A method of treatment may include selecting, identifying, recommending a scaffold that becomes malleable (through a drop in molecular weight causing a reduction in radial strength and the development of strut discontinuities) along with neointimal growth within a selected time frame to provide stabilization of lumen area during the time frame. The range of Mn at onset of or during enlargement may be less than 50 kDa, 40 kDa, 30 kDa, 20 kDa, 20 to 50 kDa, 30 to 40 kDa, or 20 to 40 kDa. The range of radial strength at onset of or during enlargement may be less than 700, less than 500 mm Hg, less than 300 mm Hg, less than 100 mm Hg, less than 30 mm Hg; 300 to 500 mm Hg, or 200 to 700 mm Hg. Stabilization means a change in lumen area, mean lumen area, or minimal lumen area by less than 20%, 10%, 5%, 1% or within 0.1 to 1%, 1 to 5%, or 5 to 10% over a time period post-deployment of 1 to 2 years, 1.5 to 3 years, 1 to 3 years, 1 to 4 years, 1 to 5 years, 1.5 to 4 years, 2 to 3 years, 2 to 5 years, or 3 to 5 years.

The time period of enlargement or start thereof may depend on the degradation rate of the scaffold since a faster degrading scaffold may reach the radial strength ranges, molecular weight ranges, or develop discontinuities sooner than one than one that degrades slower. The time period post-deployment may be greater than 3 months, greater than 6 months, greater than 9 months, 3 to 6 months, 6 to 9 months, 9 to 12 months, 12 months, greater than 18 months, greater than 24 months, 12 months to 36 months, or 18 to 36 months.

The preclinical studies demonstrated the full disappearance of the polylactide (gel permeation chromatography) at 2 years with the first generation of the Absorb BVS and at 3 years with the second generation. During that phase giant cell and granuloma can be observed in the vicinity of the struts and may explain the increase in plaque media in humans between the post procedure, the 6-month and 2 year follow-up. During that phase, the void previously occupied by the polymer is replaced by provisional matrix of proteoglycan that is going to be ultimately cellularized by connective tissues. The polylactide and the provisional matrix equally reflect the light and the struts are thus still visible on OCT at 3 years with the second generation Absorb. At 3 years, granuloma and giant cells have completely disappeared in the histology of the porcine coronary artery implanted with the second generation Absorb and may explain the (pseudo)regression of the plaque behind the struts on IVUS in humans between 2 and 3 years. A similar process of pseudo regression in Cohort A has been previously described (Sarno et al. CCI 2010).

However, future tissue evolution has to be considered: shrinking of the de novo connective tissue that has filled the original footprint of the struts will result in further thinning of the vessel wall as seen in the preclinical studies. Wall thinning may impact on lumen enlargement and/or adaptive constrictive remodeling.

The IVUS confirms this outward displacement of the struts between one and 2 years, evolving in parallel with a plaque increase and outward expansive remodeling. During the third year, the plaque and EEM regress without further changes of the mean lumen and scaffold area. This observation exemplifies the dynamics of vessel wall changes following the implantation of a bioresorbable scaffold that may induce a transient inflammatory process.

Between 1 and 3 years a significant increase in mean lumen area on IVUS was detected, with no changes in minimum lumen area, whereas on OCT an unchanged minimal and mean lumen area was seen. Lumen areas of native coronary arteries as measured by IVUS have been shown to be larger than the same areas measured by OCT, a difference that could be attributed to differences in resolution and in the physics of backscattering of ultrasound and light from in-vivo tissue. When compared (n=19), the analysis of luminal areas over time is made more complex by the differences of the two techniques (FIG. 8).

Figure 8:
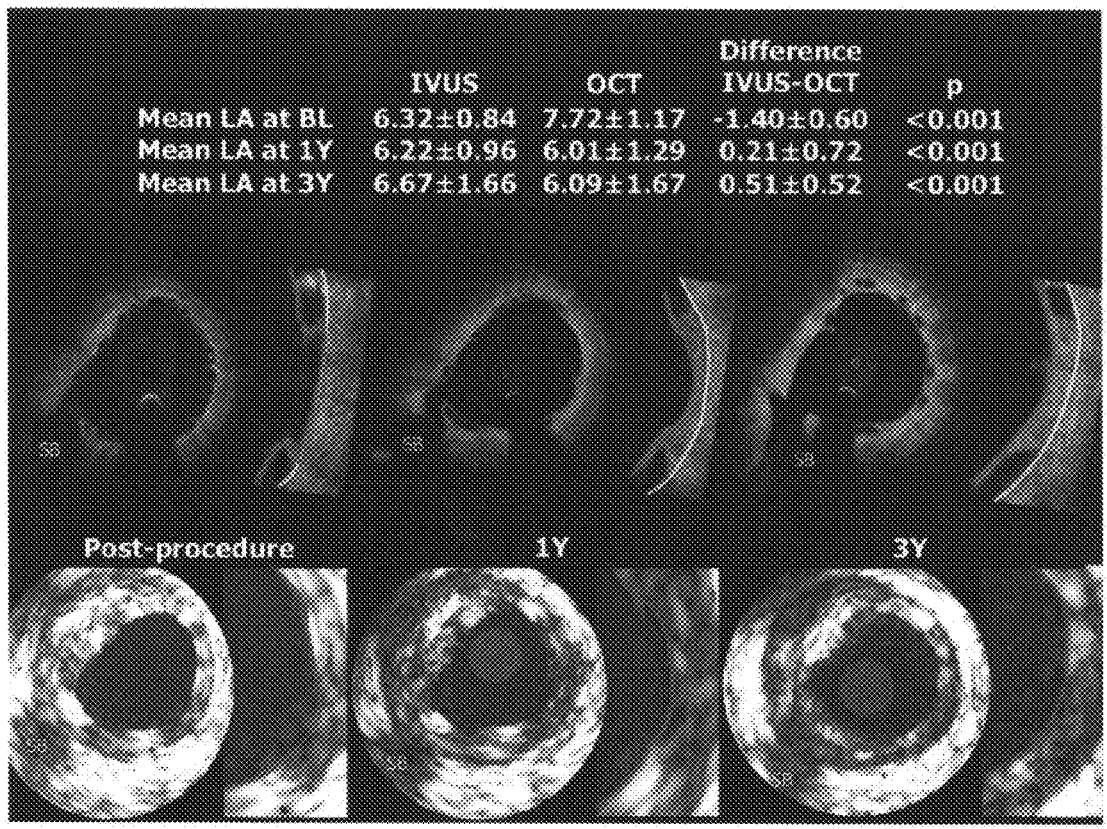
FIG. 8 shows corresponding OCT and IVUS cross section and side branch images of 19 patients who had undergone both IVUS and OCT investigation.

FIG. 8 shows corresponding OCT and IVUS cross sections and side branch images of 19 patients who had undergone both IVUS and OCT investigation. The IVUS (20 MHz) primarily detected the highly reflective endoluminal surface of the polymeric struts, and is unable to detect with precision the endoluminal contour of the vessel wall between polymeric struts apposed but not embedded in the vessel wall. In other words, the delineation of the luminal contour on IVUS after scaffold implantation relies mainly on the bright interface created by the presence of polymeric struts. In contrast, the luminal dimension as measured by OCT truly reflects and delineates the endoluminal interface of the vessel wall behind the polymeric struts: the polymeric struts do not create abluminal shadows allowing the detection of luminal contours behind the struts. At follow-up, neointimal tissue grows between polymeric struts and covers the top of the polymeric struts; this neointimal tissue (in between and on top of struts) is detectable by OCT, showing the struts encapsulated by the neointima, whereas the lumen boundaries detected by IVUS were mainly determined by the blooming brightness of the polymeric struts that has not been resorbed. This basic difference in the detection of the "luminal contour" is dynamically affected at follow-up by tissue growth as illustrated in the figure and potentially explains the absence of changes in minimal lumen area (between 1 to 3 years) as assessed by OCT, vs. the increase in mean lumen area seen in IVUS. This basic difference in detection of "luminal contour" is dynamically affected at follow-up as illustrated in FIG. 8 and explains the absence of changes in mean lumen area (between 1 to 3 years) as assessed by OCT, in contrast to the increase in mean lumen area on IVUS.

Figure 6A:
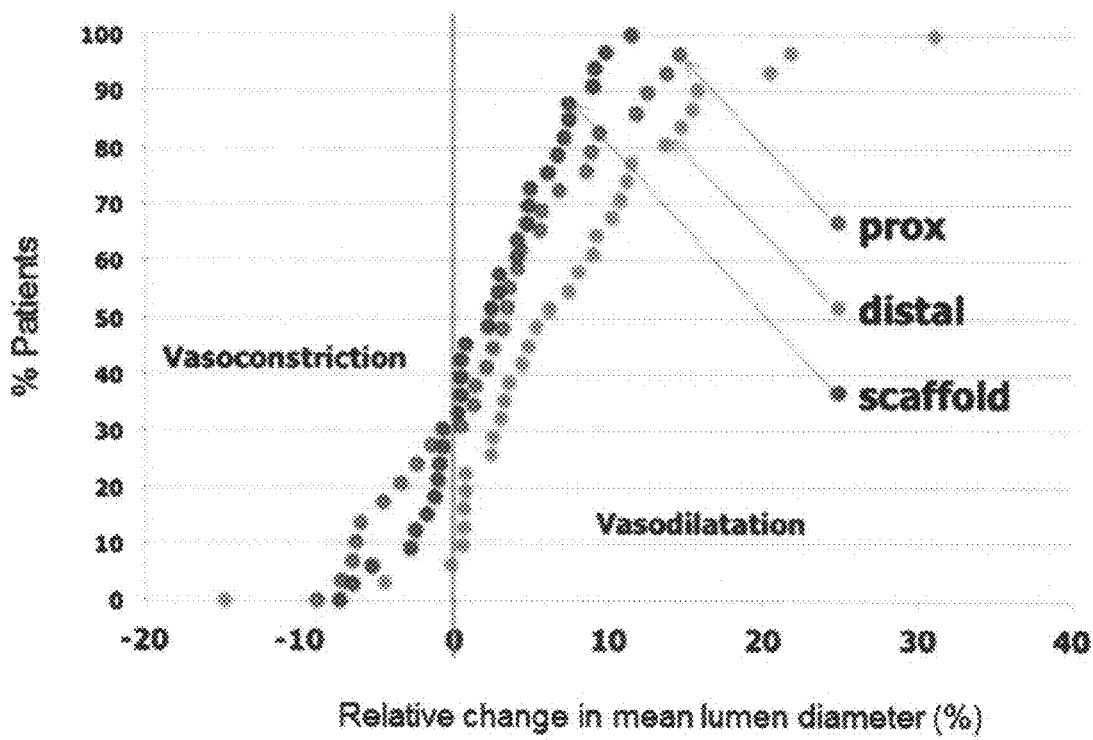
FIG. 6A depicts cumulative frequency distribution curves of relative changes (%) of mean lumen diameter after nitrate administration in the proximal, scaffold, and distal segments at 3 years.

The QCA values described in table 7 were obtained post intracoronary administration of nitrate with the exception of one patient who did not receive nitrate. FIG. 6A depicts cumulative frequency distribution curves of relative changes (%) of mean lumen diameter after nitrate administration in the proximal, scaffold, and distal segments at 3 years, where relative change=100×(mean LD post Nitrate—mean LD pre Nitrate)/mean LD pre Nitrate.

Figure 6B:
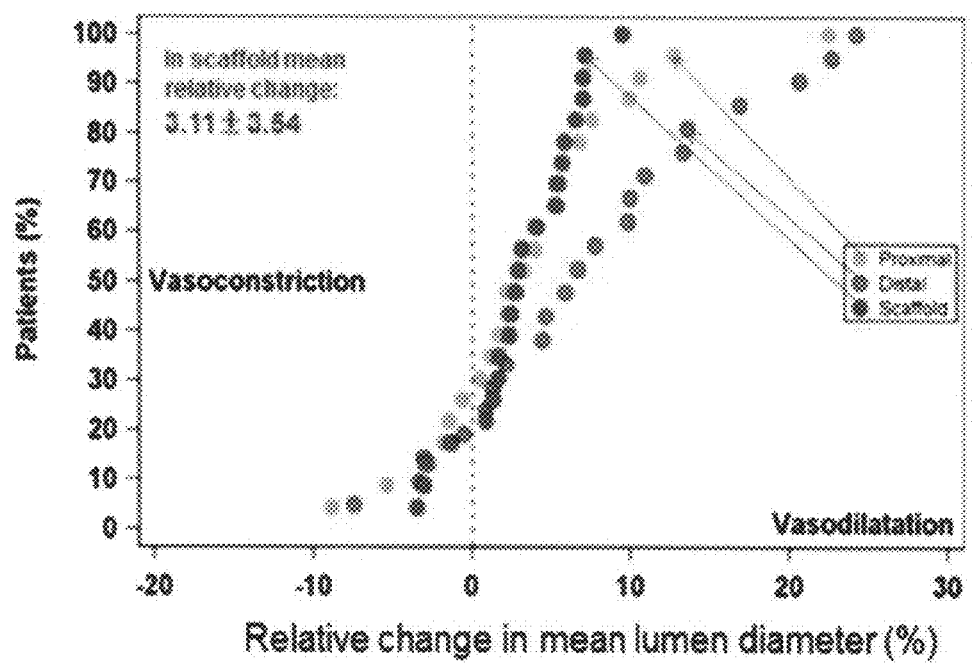
FIG. 6B depicts cumulative frequency distribution curves of relative changes (%) of mean lumen diameter after nitrate administration in the proximal, scaffold, and distal segments at 5 years.

FIG. 6B depicts cumulative frequency distribution curves of relative changes (%) of mean lumen diameter after nitrate administration in the proximal, scaffold, and distal segments at 5 years. At 5 years all patients demonstrated some degree of nitrate induced vasomotion in the scaffolded segment.

The absolute and relative changes in mean lumen diameter of the scaffold are somewhat smaller than the changes observed in the proximal or distal segments. In this phase of trial, the investigators were requested to record the blood pressure pre and post nitrate and to wait for normalization of the blood pressure and finally to reverse the decrease in blood pressure by volume expander if required. Notwithstanding, about 30% of the proximal segments and scaffold segments vasoconstricted, a phenomenon which may be attributed to the baroreceptor activation with a reflex increase in sympathetic tone and release of nor-epinephrine with secondary stimulation of alpha-1 receptors of the coronary vasculature.

The restoration of the vasodilatory capacity seems to be an ongoing process over time; at 6 months no significant vasomotion could be documented in a sequential test combining ergonovine and nitrates; at one year significant changes in vasoconstriction and vasodilatation were observed during the same test; at 2 years, only intracoronary administration of nitrate was performed and a significant ($p=0.035$) but modest ($0.034\pm0.09$ mm) vasodilatation was observed; at 3 years, the vasodilatation was accentuated ($0.054\pm0.12$ mm) and the overall effect was highly significant ($p=0.005$).

In cases with (6M: 0.19, 1Y: 0.27, 2Y: 0.27 to 3Y: 0.29, $p=1.00$) or without TLR (6M: 0.16, 1Y: 0.22, 2Y: 0.27, 3Y: 0.20 mm, $p=0.86$), there was no change in the late loss between 1 and 3 years. Cumulative frequency distribution curves of late loss at 1 and 3 years showed almost perfect superimposition of the two curves in their mid-portion (FIG. 3); out of 10 patients showing a negative loss at one year, 7 actually increased their negative late loss (or showed positive late gain) at 3 years. In all these cases, the positive late gain was not associated with malapposition of the struts on OCT.

In the entire population (n=101), the binary in-segment restenosis rate was 6%. ID-TLR was 7%: one patient received a metallic stent without binary in-segment restenosis, but for a new lesion located 10 mm distal to the scaffold; the re-PCI was adjudicated as ID-TLR, since the implanted metallic stent overlapped the previously implanted Absorb scaffold.

In Cohort B1, there were 2 cases of in-segment restenosis. In Cohort B2, there were four in-segment restenoses; one patient had a combination of in-scaffold and edge restenosis (see table 3).

There were 2 very late (after one year, at 833 and 576 days) binary in-scaffold restenoses with ischemic evidence and subsequent TLR treated with a metallic drug-eluting stent occurring between one and three years (at 833 and 569 days) for which there is no etiological explanation. In both cases, intravascular imaging confirmed the growth of neointimal tissue inside the scaffold, which was in no means crushed or encroached by a growing plaque located outside the scaffold. These very late restenosis are not a new diagnostic entity: very late restenoses have been also documented after one year in metallic everolimus eluting stents. In the SPIRIT II trial, 97 patients had serial angiographic QCA at 6 and 24 months; 7 lesions exhibited an increase in late loss (LL) of at least 0.8 mm between these two serial follow-up examinations (from −0.34, 0.37, −0.35, 0.37, −0.18, 0.08 mm to 1.15, 1.66, 0.66, 1.28, 0.63, 0.88 mm, respectively). In the SPIRIT II trial, only two patients had ischemia driven TLR; one experienced very late stent thrombosis resulting in a non-q-wave myocardial infarction between day 700 and 721 and one underwent an ID-TLR at day 701.

For this comparison 227 patients were selected from the SPIRIT I, II and III trials on the basis of a single implanted device with identical length and diameter (3.0×18 mm). This comparison should be viewed as a preamble to the ongoing randomized, ABSORB II trial, of which enrollment has recently been completed. More sophisticated adjusted comparisons using Cox regression analysis or propensity matching were precluded by the limited number of patients and events available and this analysis should be viewed as hypothesis generating.

Table 12 shows the patients at risk for time indices for Absorb Cohort B and Xience V in the Spirit clinical trials.

TABLE 12

Patients at risk in Absorb Cohort B and Xience V clinical trials.
Time After Index Procedure (days)

|  | 0 | 37 | 194 | 284 | 393 | 573 | 758 | 1123 | 1488 |
|---|---|---|---|---|---|---|---|---|---|
| ABSORB BVS (B1 + B2) at risk | 101 | 99 | 96 | 96 | 94 | 92 | 91 | 88 | 86 |
| XV(3.0 × 18 mm subgroup, SPII + SPIII RCT) at Risk | 227 | 224 | 219 | 211 | 204 | 202 | 191 | 182 | 174 |

P-values are not from formal hypotheses testing and are displayed for exploratory purposes only.

In the ABSORB Cohort B2, two patients with a myocardial bridge have been included: one with an ID-TLR at 3 months has been previously reported in great detail. The second patient had aggravation of late loss from 1 year (0.96 mm) to 3 years (1.22 mm). However this asymptomatic patient did not undergo a repeat procedure since the diameter stenosis conventionally measured on the end-diastolic angiographic frame, was 48%. In this patient, at 1 year the intracoronary administration of acetylcholine triggered a transient total occlusion which was immediately relieved by intracoronary nitrate. Currently, it is assumed that the systolic stress of a myocardial bridge on the scaffold (±110,000 cycles per day) is not compatible with an effective prevention of restenosis. It would be prudent to consider myocardial bridging as a contraindication for treatment with a bioresorbable scaffold.

The main long-term hypothesis is that late lumen enlargement will occur together with wall thinning and adaptive remodeling. Some heralding signs of these changes were detectable on IVUS: at 3 year follow-up, when compared to post procedure there is a significant increase in both mean scaffold area and mean lumen area with unchanged values of minimal scaffold area and minimal lumen area: In addition, there is a significant decrease in plaque behind scaffold area between 2 and 3 years, which is accompanied by adaptive constrictive remodeling of the vessel area between 2 and 3 years (Tables 8A and 8B and FIG. 5).

This would suggest that the expansive remodeling process observed in the first 2 years has been halted and followed by a plaque (pseudo)regression between the second and third year with constriction of the EEM, suggesting an adaptive remodeling not seen in vessels caged with metallic stents.

Figure 9:
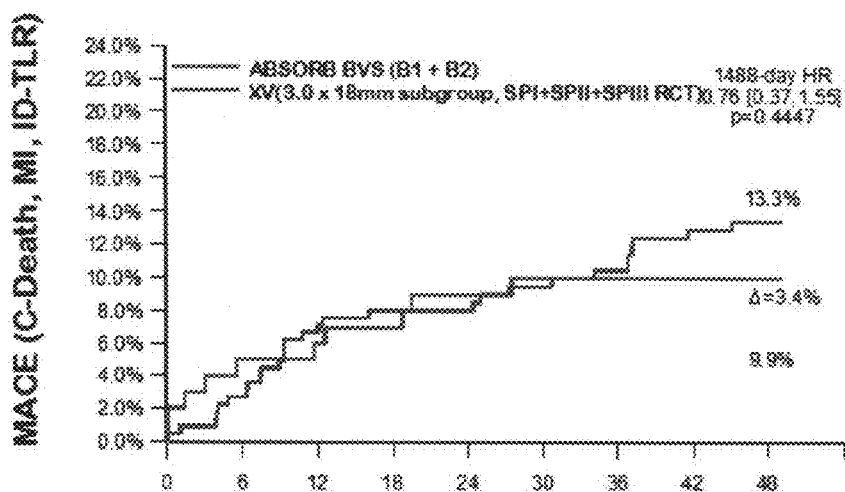
FIG. 9 depicts Kaplan-meier estimates of cumulative major adverse cardiac events (cardiac mortality, any myocardial infarction or ischemia-driven target lesion revascularization) of the Absorb Cohort B (red, n=101) and the 226 patients who received a single 3.0×18 mm metallic everolimus eluting stent in the SPIRIT I, II and III trials (blue).

The preliminary non-randomized comparison of clinical outcomes for the Absorb BVS scaffold and the XIENCE V metallic stent shows that these two devices have similar event rates up to 3 years (FIG. 9). FIG. 9 depicts Kaplan-meier estimates of cumulative major adverse cardiac events (cardiac mortality, any myocardial infarction or ischemia-driven target lesion revascularization) of the ABSORB Cohort B (red, n=101) and the 226 patients who received a single 3.0×18 mm metallic everolimus eluting stent in the SPIRIT I, II, and III trials (blue).

The 4-year data reported for the Absorb BVS demonstrates its favorable and stable long-term performance and safety. In particular, there were no additional MACE between 3 and 4 years with a stable rate of 10% at 4 years there were no scaffold thrombosis events out to 4 years. In comparison to XIENCE V in SPIRIT I, II and III, the ABSORB BVS patients in Cohort B had no additional MACE events from 28 months up to 4 year follow-up.

The current analysis is limited in the fact that invasive imaging follow-up was sometimes not performed at one and 3 years. Six patients did not undergo angiography at 3 years, these patients had no events. In the angiographic analysis, however, pre-TLR minimal lumen diameter (therefore the worst MLD) was measured in all event cases and those values are used as the MLD at 3 years. The MLD data derived from the current analysis are therefore still representative of the overall temporal changes in lumen dimensions. Conversely, in the patients who underwent TLR, pre-TLR IVUS or OCT are missing in 3 and 2 patients respectively. The IVUS and OCT analysis might therefore under-represent the changes in lumen dimensions.

The prevailing mechanism of degradation of many bioabsorbable polymers is chemical hydrolysis of the hydrolytically unstable backbone. In a bulk degrading polymer, the polymer is chemically degraded throughout the entire polymer volume. As the polymer degrades, the molecular weight decreases. The reduction in molecular weight results in changes in mechanical properties (e.g., strength) and stent properties. For example, the strength of the scaffold material and the radial strength of the scaffold are maintained for a period of time followed by a gradual or abrupt decrease. The decrease in radial strength is followed by a loss of mechanical integrity and then erosion or mass loss. Mechanical integrity loss is demonstrated by cracking and by fragmentation. Enzymatic attack and metabolization of the fragments occurs, resulting in a rapid loss of polymer mass.

The behavior of a bioabsorbable stent upon implantation can divided into three stages of behavior. In stage I, the stent provides mechanical support. The radial strength is maintained during this phase. Also during this time, chemical degradation occurs which decreases the molecular weight. In stage II, the scaffold experiences a loss in strength and mechanical integrity. In stage III, significant mass loss occurs after hydrolytic chain scission yields water-soluble low molecular weight species.

The scaffold in the first stage provides the clinical need of providing mechanical support to maintain patency or keep a vessel open at or near the deployment diameter. In some treatments, the patency provided by the scaffold allows the stented segment of the vessel to undergo positive remodeling at the increased deployed diameter. Remodeling refers generally to structural changes in the vessel wall that enhances its load-bearing ability so that the vessel wall in the stented section can maintain an increased diameter in the absence of the stent support. A period of patency is required in order to obtain permanent positive remodeling.

The manufacturing process of a bioabsorbable scaffold includes selection of a bioabsorbable polymer raw material or resin. Detailed discussion of the manufacturing process of a bioabsorbable stent can be found elsewhere, e.g., U.S. Patent Publication No. 20070283552. The fabrication methods of a bioabsorbable stent can include the following steps:

(1) forming a polymeric tube from a biodegradable polymer resin using a method such as extrusion, injection molding, spraying a polymer solution over a mandrel, or dipping a mandrel into a polymer solution (2) processing the tube to increase radial strength which can include annealing above a Tg of the polymer, radially deforming the tube above the Tg of the polymer, or both, (3) forming a stent scaffolding from the processed tube by laser machining a stent pattern in the deformed tube with laser cutting, in exemplary embodiments, the strut thickness can be 100-200 microns, or more narrowly, 120-180, 130-170, or 140-160 microns, (4) optionally forming a therapeutic coating over the scaffolding, (5) crimping the stent over a delivery balloon, and (6) sterilization with electron-beam (E-beam) radiation.

Poly(L-lactide) (PLLA) is attractive as a stent material due to its relatively high strength and rigidity at human body temperature, about 37° C. Since it has a glass transition temperature between about 60 and 65° C. (Medical Plastics and Biomaterials Magazine, March 1998), it remains stiff and rigid at human body temperature. This property facilitates the ability of a PLLA stent scaffold to maintain a lumen at or near a deployed diameter without significant recoil (e.g., less than 10%). In general, the Tg of a semicrystalline polymer can depend on its morphology, and thus how it has been processed. Therefore, Tg refers to the Tg at its relevant state, e.g., Tg of a PLLA resin, extruded tube, expanded tube, and scaffold.

In general, a scaffold can be made of a bioresorbable aliphatic polyester. Additional exemplary biodegradable polymers for use with a bioabsorbable polymer scaffolding include poly(D-lactide) (PDLA), poly(L-lactide-co-caprolactone), polymandelide (PM), polyglycolide (PGA), poly (L-lactide-co-D,L-lactide) (PLDLA), poly(D,L-lactide) (PDLLA), poly(D,L-lactide-co-glycolide) (PLGA) and poly (L-lactide-co-glycolide) (PLLGA).

With respect to PLLGA, the stent scaffolding can be made from or include PLLGA with a mole % of GA between 5-15 mol %. The PLLGA can have a mole % of (LA:GA) of 85:15 (or a range of 82:18 to 88:12), 95:5 (or a range of 93:7 to 97:3), or commercially available PLLGA products identified as being 85:15 or 95:5 PLLGA. The examples provided above are not the only polymers that may be used. Many other examples can be provided, such as those found in Polymeric Biomaterials, second edition, edited by Severian Dumitriu; chapter 4.

The scaffold polymer, coating polymer, or both may include a polylactide (PLA)-based polymer or polymer combination (blend, copolymer, or copolymer blend). A PLA-based polymer may correspond to a polymer or polymer combination with a total lactide composition of greater than 90%, greater than 95%, greater than 98%, 90 to 98%, 90 to 95%, or 95 to 98% in wt or mol %. The lactide can be L-lactide, d-lactide, mesolactide, or any combination thereof.

Polymers that are more flexible or that have a lower modulus than those mentioned above may also be used. Exemplary lower modulus bioabsorbable polymers include, polycaprolactone (PCL), poly(trimethylene carbonate) (PTMC), polydioxanone (PDO), poly(4-hydroxy butyrate) (PHB), and poly(butylene succinate) (PBS), and blends and copolymers thereof.

The molecular weight of a scaffold prior to implantation in number or weight average molecular weight can be 70 to 150 kDa, 70 to 80 kDa, 80 to 90 kDa, 90 to 100 kDa, 100 to 110 kDa, 110 to 120 kDa, 120 to 150 kDa, 70 kDa, 80 kDa, 90 kDa, 100 kDa, or 110 kDa.

In exemplary embodiments, higher modulus polymers such as PLLA or PLLGA may be blended with lower modulus polymers or copolymers with PLLA or PLGA. The blended lower modulus polymers result in a blend that has a higher fracture toughness than the high modulus polymer. Exemplary low modulus copolymers include poly(L-lactide)-b-polycaprolactone (PLLA-b-PCL) or poly(L-lactide)-co-polycaprolactone (PLLA-co-PCL). The composition of the blend can include 1-5 wt % of low modulus polymer.

The scaffolds may be coated with a polymer mixture that includes Everolimus, an antiproliferative agent. In general, the anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin II, actinomycin X1, and actinomycin C1), all taxoids such as taxols, docetaxel, and paclitaxel, paclitaxel derivatives, novolimus, myolimus, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy) propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof.

An anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, codrugs thereof, and combinations thereof.

These agents can also have anti-proliferative and/or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable. The scaffold can exclude any of the drugs disclosed herein.

"Baseline" refers to a time immediately after deployment of a scaffold to a target diameter in a vessel or at a time after deployment long enough to make measurements on the newly deployed scaffold. Unless otherwise specified, a time period such as 6 months, 1 year, 2 years, or 3 years refers to a time period passed from baseline or deployment.

The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. $T_g$ of a given polymer can be dependent on the heating rate and can be influenced by the thermal history of the polymer as well as its degree of crystallinity. Furthermore, the chemical structure of the polymer heavily influences the glass transition by affecting mobility.

The $T_g$ can be determined as the approximate midpoint of a temperature range over which the glass transition takes place. [ASTM D883-90]. The most frequently used definition of $T_g$ uses the energy release on heating in differential scanning calorimetry (DSC). As used herein, the $T_g$ refers to a glass transition temperature as measured by differential scanning calorimetry (DSC) at a 20° C./min heating rate.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus typically is the initial slope of a stress—strain curve at low strain in the linear region.

The current investigation demonstrated the dynamism of vessel wall changes after implantation of an Absorb bioresorbable scaffold, resulting at 3 years in stable luminal dimensions, a low restenosis rate and low clinical major adverse cardiac event rates.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A method of reducing plaque at a segment of a coronary blood vessel comprising an implanted bioabsorbable scaffold in a patient being treated for atherosclerosis, comprising:
deploying a bioabsorbable scaffold composed of a plurality of interconnected struts at a stenotic segment of an artery of a patient having a plaque burden, wherein the struts consist of a bioabsorbable backbone or core surrounded by a single layer of an amorphous drug eluting coating matrix that is a mixture of a poly(D, L-lactide) (PDLLA) polymer and an anti-proliferative drug which is released from the coating matrix upon deployment of the scaffold, wherein a thickness of the struts is 140 to 160 microns and a thickness of the layer of the coating matrix is 2 to 2.5 microns,
wherein after a period of supporting the segment, the scaffold becomes malleable due to a reduction in radial strength and dismantling of the scaffold caused by biodegradation of the scaffold; and
administering a plaque burden reducing medication to the patient to reduce the plaque burden between the malleable scaffold and vessel media, the administration made after onset of outward compensatory enlargement of the vessel which starts at about 1 year after deployment of the scaffold, the outward compensatory enlargement prevents malapposition between the malleable scaffold and the vessel media due to outward displacement of the malleable scaffold as the vessel enlarges.

2. The method of claim 1, wherein the backbone or core bioabsorbable polymer is a PLA-based polymer.

3. The method of claim 1, wherein the plaque burden reducing medication comprises a statin.

4. The method of claim 1, wherein the scaffold polymer is replaced by a provisional matrix comprising proteoglycan as it biodegrades.

5. The method of claim 1, wherein the compensatory enlargement starts at 1 year or about 1 year after deployment of the scaffold.

6. The method of claim 1, wherein the compensatory enlargement starts at a time when the number average molecular weight (Mn) of the backbone or core bioabsorbable polymer is less than about 50 kDa.

7. The method of claim 1, wherein the enlargement starts when radial strength is less than 400 mm Hg.

8. The method of claim 1, wherein the plaque burden reducing medication is selected from the group consisting of rosuvastatin, atorvastatin, fluvastatin, and lovastatin.

9. The method of claim 1, wherein the scaffold becomes covered by a neointimal layer prior to the dismantling.

10. The method of claim 1, wherein the enlargement of the vessel comprises an increase in the external elastic membrane (EEM) of the vessel.

* * * * *

UNITED STATES PATENT AND TRADEMARK OFFICE
CERTIFICATE OF CORRECTION

| | |
|---|---|
| PATENT NO. | : 10,143,572 B2 |
| APPLICATION NO. | : 14/121435 |
| DATED | : December 4, 2018 |
| INVENTOR(S) | : Rapoza et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 746 days.

Signed and Sealed this
Tenth Day of September, 2019

Andrei Iancu
*Director of the United States Patent and Trademark Office*